US008645083B2

(12) United States Patent
Schraeml et al.

(10) Patent No.: US 8,645,083 B2
(45) Date of Patent: Feb. 4, 2014

(54) METHOD TO SCREEN HIGH AFFINITY ANTIBODY

(75) Inventors: Michael Schraeml, Penzberg (DE); Leopold Von Proff, Hohenpeissenberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 35 days.

(21) Appl. No.: 13/060,535

(22) PCT Filed: Aug. 25, 2009

(86) PCT No.: PCT/EP2009/006136
§ 371 (c)(1),
(2), (4) Date: Feb. 24, 2011

(87) PCT Pub. No.: WO2010/022910
PCT Pub. Date: Mar. 4, 2010

(65) Prior Publication Data
US 2011/0160436 A1     Jun. 30, 2011

(30) Foreign Application Priority Data

Aug. 27, 2008   (EP) ..................................... 08015099

(51) Int. Cl.
*G01N 31/00*     (2006.01)
*G01N 33/48*     (2006.01)
*G06G 7/58*     (2006.01)

(52) U.S. Cl.
USPC .................................. 702/27; 702/19; 703/11

(58) Field of Classification Search
None
See application file for complete search history.

(56) References Cited

FOREIGN PATENT DOCUMENTS

| JP | 2005017154 (A) | 1/2005 |
|---|---|---|
| JP | 2005513496 (A) | 5/2005 |
| JP | 2008111713 (A) | 5/2008 |
| JP | 2008513540 (A) | 5/2008 |
| WO | 03056296 A2 | 7/2003 |
| WO | 2006034292 A2 | 3/2006 |
| WO | 2006/135309 | 12/2006 |
| WO | 2007018475 A1 | 2/2007 |
| WO | 2007137984 A2 | 12/2007 |

OTHER PUBLICATIONS

Barnes et al., "Advances in animal cell recombinant protein production: GS-NSO expression system" *Cytotechnology* 32(2):109-23 (Feb. 2000).
Barnes et al., "Characterization of the stability of recombinant protein production in the GS-NSO expression system" *Biotechnol Bioeng.* 73(4):261-70 (May 2001).
Canziani et al., "Kinetic screening of antibodies from crude hybridoma samples using Biacore" *Analytical Biochemistry* 325(2):301-7 (Feb. 2004).
Carter et al., "Humanization of an Anti-p185$^{HER2}$ Antibody for Human Cancer Therapy" *Proc Natl Acad Sci U S A.* 89(10) :4285-4289 (May 1992).
Chaires, "Calorimetry and thermodynamics in drug design" *Annu Rev Biophys.* 37:135-51 (2008).
Drake et al., "Characterizing high-affinity antigen/antibody complexes by kinetic- and equilibrium-based methods" *Analytical Biochemistry* 328(1):35-43 (2004).
Durocher et al., "High-level and high-throughput recombinant protein production by transient transfection of suspension-growing human 293-EBNA1 cells" *Nucleic Acids Research* 30(2):E9 (2002).
Geisse et al., "Eukaryotic Expression Systems: A Comparison" *Protein Expression and Purification* 8:271-282 (1996).
Gunnarsson, "Affinity-based biosensors for biomolecular interaction analysis" *Curr Protoc Immunol.* (Chapter 18:Unit 18.6.) (2001).
Kaufman, "Overview of Vector Design for Mammalian Gene Expression" *Molecular Biotechnology* 16:151-160(2000).
Kikuchi et al., "Determination of concentration and binding affinity of antibody fragments by use of surface plasmon resonance" *J Biosci Bioeng.* 100(3):311-7 (Sep. 2005).
Kohler and Milstein, "Continuous Cultures of Fused Cells Secreting Antibody of Predefined Specificity" *Nature* 256(5517):495-497 (Aug. 7, 1975).
Leonard et al., "High throughput ranking of recombinant avian scFv antibody fragments from crude lysates using the Biacore A100" *J Immunol Methods* 323(2):172-9 (Jun).
Li et al., "PDBcal: a comprehensive dataset for receptor-ligand interactions with three-dimensional structures and binding thermodynamics from isothermal titration calorimetry" *Chem Biol Drug Des.* 71(6):529-32 (Jun. 2008).

(Continued)

*Primary Examiner* — Eric S Dejong
(74) *Attorney, Agent, or Firm* — Y. Elaine Chang

(57) ABSTRACT

The current invention reports a method for producing an antibody comprising the steps of a) providing a plurality of hybridoma cells each expressing an antibody, b) determining the time dependent amount of said antibody bound to the respective antigen by surface plasmon resonance at different temperatures and different antibody concentrations, c) calculating with the time dependent amount determined in b) based on equations (II) to (XIII) at least the thermodynamic parameters (i) standard association binding entropy formula (A), (ii) standard dissociation binding entropy formula (B), (iii) standard binding entropy ($\Delta S°$), (iv) free standard binding enthalpy ($\Delta G°$), (v) standard dissociation free binding enthalpy formula (C), (vi) standard association free binding enthalpy formula (D), (vii) $-T\Delta S°$, (viii) dissociation rate constant $k_d$, (ix) equilibrium binding constant $K_D$, and (x) association rate constant $k_a$, d) selecting a hybridoma cell producing an antibody with at least two of the following: i) a standard association binding entropy of less than 10 J/K*mol, ii) an absolute standard dissociation binding entropy of 100 J/mol*K or more, iii) an absolute standard binding entropy of 100 J/mol*K or more, e) producing an antibody by cultivating said selected cell under conditions suitable for the expression of said antibody and recovering said antibody from the cells or/and the cultivation medium.

4 Claims, 15 Drawing Sheets

(56) References Cited

OTHER PUBLICATIONS

Liang, "Applications of isothermal titration calorimetry in protein science" *Acta Biochim Biophys Sin (Shanghai)* 40(7):565-76 (Jul. 2008).

Makrides, S.C., "Components of Vectors for Gene Transfer and Expression in Mammalian Cells" *Protein Expression and Purification* 17:183-202 (1999).

Naghibi et al., "Significant discrepancies between van't Hoff and calorimetric enthalpies" *Proc Natl Acad Sci U S A*. 92(12):5597-9 (Jun. 1995).

Norderhaug et al., "Versatile Vectors for Transient and Stable Expression of Recombinant Antibody Molecules in Mammalian Cells" *Journal of Immunological Methods* 204:77-87 (1997).

Orlandi et al., "Cloning Immunoglobulin Variable Domains for Expression by the Polymerase Chain Reaction" *Proc. Natl. Acad. Sci. USA* 86:3833-3837 (May 1989).

Perozzo et al., "Thermodynamics of protein-ligand interactions: history, presence, and future aspects" *J. Recept Signal Transduct Res.* 24(1-2):1-52 (Feb. 2004).

Presta et al., "Generation of a Humanized, High Affinity Anti-Tissue Factor Antibody for Use as a Novel Antithrombotic Therapeutic" *Thrombosis and Haemostasis* 85(3):379-389 (Mar. 2001).

Rich et al., "Higher-throughput, label-free, real-time molecular interaction analysis" *Analytical Biochemistry* 361(1):1-6 (Feb. 2007).

Roos et al., "Thermodynamic analysis of protein interactions with biosensor technology" *J Mol Recognit*. 11(1-6):204-10 (1998).

Safsten et al., "Screening antibody-antigen interactions in parallel using Biacore A100" *Analytical Biochemistry* 353(2):181-90 (Jun. 2006).

Schlaeger et al., "Transient Gene Expression in Mammalian Cells Grown in Serum-free Suspension Culture" *Cytotechnology* 30:71-83 (1999).

Schlaeger, "The Protein Hydrolysate, Primatone RL, is a Cost-effective Multiple Growth Promoter of Mammalian Cell Culture in Serum-containing and Serum-free Media and Displays Anti-apoptosis Properties" *Journal of Immunological Methods* 194:191-199 (1996).

Steukers et al., "Rapid kinetic-based screening of human Fab fragments" *J Immunol Methods* 310(1-2):126-35 (Mar. 2006).

Tellinghuisen, "Van't Hoff analysis of K degrees (T): how good . . . or bad?" *Biophys Chem*. 120(2):114-20 (Mar. 2006).

Thielges et al., "Exploring the energy landscape of antibody-antigen complexes: protein dynamics, flexibility, and molecular recognition" *Biochemistry* 47(27):7237-47 (2008).

Thorpe et al., "Molecular evolution of affinity and flexibility in the immune system" *Proc Natl Acad Sci U S A*. 104(21):8821-6 (May 2007).

Van Regenmortel et al., "Measurement of antigen-antibody interactions with biosensors" *J Mol Recognit*. 11(1-6):163-7 (1998).

Wassaf et al., "High-throughput affinity ranking of antibodies using surface plasmon resonance microarrays" *Analytical Biochemistry* 351(2):241-53 (Apr. 2006).

Wear et al., "Thermodynamics of the cyclophilin-A/cyclosporin-A interaction: a direct comparison of parameters determined by surface plasmon resonance using Biacore T100 and isothermal titration calorimetry" *Analytical Biochemistry* 359(2):285-7 (Dec. 2006).

Werner et al., "Appropriate mammalian expression systems for biopharmaceuticals" *Arzneimittel-Forschung (Drug Res.)* 48(8):870-880 (1998).

Zhukov et al., "Statistical aspects of van't Hoff analysis: a simulation study" *J Mol Recognit*. 20(5):379-85 (2007).

EPO Communications dated Jul. 10, 2013 in Appl 09809290.1 filed Aug. 25, 2009.

Willuda, J. et al. et al., "High thermal stability is essential for tumor targeting of antibody fragments: enineering of a humanized anti-epithelial glycoprotein-2 (Epithelial Cell Adhesion Molecule) single-chain Fv fragment" *Cancer Res* 59:5758-5767 (Nov. 15, 1999).

METHOD TO SCREEN HIGH AFFINITY ANTIBODY

CROSS-REFERENCE TO RELATED APPLICATIONS

This application is made under 35 US §371 based on International Application PCT/EP2009/006136 filed on Aug. 25, 2009, and claims the benefit of priority of European patent application number 08015099.8 filed Aug. 27, 2008, the contents of both of which are incorporated herein by reference in their entirety.

Herein is reported a method for the determination of a high affinity antibody based on thermodynamic parameters of the antibody, especially transition state thermodynamics to evaluate the binding entropy such as the standard association binding entropy ($\Delta S°\ddagger ass$) and the entropic burden during the antigen binding step.

BACKGROUND OF THE INVENTION

The generation of high-affinity antibodies with distinguished antigen specificity and extraordinary antigen complex stability is a major goal in diagnostic and therapeutic antibody development.

Regarding thermodynamic analyses of protein-protein interactions the prevailing technology is the calorimetric assay (Chaires, J. B., Annu. Rev. Biophys. 37 (2008) 135-51; Perozzo, R., et al., J. Recept. Signal Transduct. Res. 24 (1-2) (2004) 1-52; Li, L., et al., Chem. Biol. Drug Des. 71(6) (2008) 529-32; Liang, Y., Acta Biochim. Biophys. Sin. (Shanghai) 40(7) (2008) 565-76; Thielges, M. C., et al., Biochemistry 47(27) (2008) 7237-47). The required sample amount for a reaction calorimeter determination is high, such as an antibody concentration of at least 125 µg/ml and sample volumes of at least 150 µl. Furthermore reaction calorimetry requests high sample purity and does not tolerate any sample impurities or sample heterogeneity and the sample buffers directly influence the results of the thermodynamic parameters results. Reaction calorimetry is solely able to resolve equilibrium thermodynamics.

Surface Plasmon Resonance (SPR) instrumentation (Roos, H., et al., J. Mol. Recognit. 11(1-6) (1998) 204-10; Van Regenmortel, M. H., et al., J. Mol. Recognit. 11(1-6) (1998) 163-7; Gunnarsson, K., Curr. Protoc. Immunol. Chapter 18 (2001) Unit 18.6; Drake, A. W., et al., Anal. Biochem. 328(1) (2004) 35-43; Kikuchi, Y., et al., J. Biosci. Bioeng. 100(3) (2005) 311-7) allows the rapid determination of temperature-dependent kinetic profiles in a high throughput manner (see e.g. Canziani, G. A., et al., Anal. Biochem. 325(2) (2004) 301-7; Safsten, P., et al., Anal. Biochem. 353(2) (2006) 181-190; Leonard, P., et al., J. Immunol. Methods 323(2) (2007) 172-9).

Wassaf, D., et al. (Anal. Biochem. 351 (2006) 241-253) report high-throughput affinity ranking of antibodies using surface plasmon resonance microarrays. A thermodynamic analysis of protein interactions with biosensor technology is reported in Roos, H., et al., J. Mol. Recognit. 11 (1998) 204-210.

SUMMARY OF THE INVENTION

The current invention provides a method for the selection of an high affinity antibody with temperature-independent antigen complex stability, characterized by an enthalpy-driven antigen association, a negative entropic burden and a large entropy change during antigen dissociation.

A first aspect of the invention is a method for the selection of an antibody from a plurality of antibodies binding to an antigen, said method comprises the following steps:

optimizing the signal response in a surface plasmon resonance determination based on the molecular weight of the antigen, whereby $R_{max}$ is kept constant in the temperature range of the determination, performing a kinetic screening step, which comprises the calculation of an antigen-complex-stability according to formula (I)

$$\text{antigen-complex-stability} = (1 - [BL(RU) - SL(RU)]/BL(RU)]) \quad (I)$$

based on the surface plasmon resonance determination with BL denoting a Binding Late reference point set shortly before the antigen's injection ends, SL denoting a Stability Late reference point set shortly before the end of the complex dissociation phase, selecting antibodies with complex stabilities greater than 95%, determining temperature-dependent kinetic data by surface plasmon resonance, at 17° C., at 21° C., at 25° C., at 29° C., at 33° C., and at 37° C., calculating Transition State thermodynamic properties, selecting an antibody based on a temperature-dependent acceleration of the antigen complex association rate constant ka [1/Ms] and a remaining or decreasing antigen complex dissociation rate constant kd [1/s].

In one embodiment of this aspect is the generation of temperature-dependent kinetic data based on a surface plasmon resonance determination and calculation of thermodynamic properties of said antibody with a thermodynamic screening performed at 17° C. with 107 nM, at 21° C. with 78 nM, at 25° C. with 70 nM, at 29° C. with 64 nM, at 33° C. with 58 nM and at 37° C. with 53 nM antibody concentration, and/or the thermodynamic properties an enthalpy-driven $\Delta H°\ddagger ass$ antigen complex association phase and a binding entropy $\Delta S°\ddagger ass$ of less than 10 J/K*mol, and/or an antibody selected with a dissociation phase showing a negative or nearby zero dissociation activation energy (Eadiss [kJ/mol]), a negative dissociation enthalpy ($\Delta H°\ddagger diss$ [kJ/mol]), and a large negative dissociation entropy ($\Delta S°\ddagger diss$ [kJ/mol]).

One aspect of the invention is a method for producing an antibody comprising the following steps:

a) providing a plurality of cells, preferably hybridoma cells or B-cells, each expressing an antibody, b) determining the time dependent amount of said antibody bound to the respective antigen by surface plasmon resonance at different temperatures and different antibody concentrations, c) calculating with the time dependent amount determined in b) based on equations (II) to (XIII)

$$\Delta G° = \Delta H° - T^*\Delta S° \quad (II)$$

$$\Delta G° = -R^*T^* \ln K_D \quad (III)$$

$$\ln K_D = -1/T^*(\Delta H°/R)/\text{slope} - (\Delta S°/R)/\text{intercept} \quad (IV)$$

$$R^*T^* \ln K_D = \Delta H°_{T0} - T^*\Delta S°_{T0} + \Delta C°_p(T-T_0) - T^*\Delta C_p° \ln(T/T_0) \quad (V)$$

$$k_a = (k_b^* T/h)^* e^{(-\Delta G°\ddagger/R^*T)} \quad (VI)$$

$$\ln k_a/T = -1/T^*(\Delta H°\ddagger/R)/\text{slope} + (\Delta S°\ddagger^* R + \ln k_b/h)/\text{intercept} \quad (VII)$$

$$k_a = A * e^{-Ea/R*T} \quad \text{(VIII)}$$

$$\ln k_a = \ln A/\text{intercept} - (1/T*Ea/R)/\text{slope} \quad \text{(IX)}$$

$$k_d = (k_b*T/h)*e^{(-\Delta G^{\circ\ddagger}/R*T)} \quad \text{(X)}$$

$$\ln k_d/T = -1/T*(\Delta H^{\circ\ddagger}/R)/\text{slope} + (\Delta S^{\circ\ddagger}/R + \ln k_B/h)/\text{intercept} \quad \text{(XI)}$$

$$k_d = A * e^{-Ea/R*T} \quad \text{(XII)}$$

$$\ln k_d = \ln A/\text{intercept} - (1/T*Ea/R)/\text{slope} \quad \text{(XIII)}$$

at least the thermodynamic parameters
  (i) standard association binding entropy ($\Delta S^{\circ}\ddagger$ass),
  (ii) standard dissociation binding entropy ($\Delta S^{\circ}\ddagger$diss),
  (iii) standard binding entropy ($\Delta S^{\circ}$),
  (iv) free standard binding enthalpy ($\Delta G^{\circ}$),
  (v) standard dissociation free binding enthalpy ($\Delta G^{\circ}\ddagger$diss),
  (vi) standard association free binding enthalpy ($\Delta G^{\circ}\ddagger$ass),
  (vii) $-T\Delta S^{\circ}$,
  (viii) dissociation rate constant $k_d$,
  (ix) equilibrium binding constant $K_D$, and
  (x) association rate constant $k_a$,
d) selecting a cell producing an antibody with at least two of the following:
  i) a standard association binding entropy of less than 10 J/K*mol,
  ii) an absolute standard dissociation binding entropy of 100 J/mol*K or more,
  iii) an absolute standard binding entropy of 100 J/mol*K or more,
e) producing an antibody by cultivating said selected cell under conditions suitable for the expression of said antibody and recovering said antibody from the cells or/and the cultivation medium.

In one embodiment the method comprises one or both of the following additional steps:
  after a) and before b): a1) cultivating the cells of a) and providing culture supernatants each containing antibodies expressed by said cells,
  after step d) and before step e): d1) isolating the nucleic acid encoding said antibody from said selected cell, providing based on said isolated nucleic acid a further nucleic acid encoding a chimeric, CDR-grafted, T-cell epitope depleted and/or humanized variant of said antibody, providing an expression plasmid containing said modified nucleic acid in an expression cassette, and transfecting a CHO cell, a NS0 cell, a SP2/0 cell, a HEK293 cell, a COS cell, or a PER.C6 cell with said expression plasmid.

Another aspect of the current invention is a method for the selection of a temperature-independent antigen binding antibody from a plurality of antibodies, e.g. for a therapeutic treatment, whereby an antibody is selected with a standard association binding entropy ($\Delta S^{\circ}\ddagger$ass) of less than 10 J/K*mol.

In one embodiment of this aspect an antibody is selected with at least two of
  a) a standard association binding entropy ($\Delta S^{\circ}\ddagger$ass) of less than 10 J/K*mol,
  b) an absolute standard dissociation binding entropy ($\Delta S^{\circ}\ddagger$diss) of 100 J/mol*K or more,
  c) an absolute standard binding entropy ($\Delta S^{\circ}$) of 100 J/mol*K or more.

In one embodiment of the methods according to the invention the standard association binding entropy ($\Delta S^{\circ}\ddagger$ass) is of less than 5 J/K*mol. In another embodiment the standard association binding entropy ($\Delta S^{\circ}\ddagger$ass) is of less than 0 J/K*mol. In a further embodiment absolute standard dissociation binding entropy ($\Delta S^{\circ}\ddagger$diss) is of 125 J/mol*K or more. In still a further embodiment the absolute standard dissociation binding entropy ($\Delta S^{\circ}\ddagger$diss) is of 150 J/mol*K or more. In another embodiment the absolute standard binding entropy ($\Delta S^{\circ}$) is of 125 J/mol*K or more. In a further embodiment the absolute standard binding entropy ($\Delta S^{\circ}$) is of 150 J/mol*K or more.

In one embodiment of the current invention the methods are characterized in that an antibody is selected with a free standard binding enthalpy ($\Delta G^{\circ}$) of $-50$ kJ/mol or less. In a further embodiment the methods according to the invention are characterized in that an antibody is selected with a ratio of the standard dissociation free binding enthalpy ($\Delta G^{\circ}\ddagger$diss) to the standard association free binding enthalpy ($\Delta G^{\circ}\ddagger$ass) of more than 2.3. In a further embodiment the methods are characterized in that an antibody is selected with a $-T\Delta S^{\circ}$ value
  a) of $-80$ kJ/mol or less, or
  b) of $+40$ kJ/mol or more.

Another aspect of the invention is a method for the selection of a temperature-independent antigen binding antibody from a plurality of antibodies, e.g. for use in a pharmaceutical composition, comprising the step of selecting an antibody with a dissociation rate constant $k_d$ (1/s) remaining in the same order of magnitude, or decreases up to two orders of magnitude with increasing temperature.

A further aspect of the invention is a method for the selection of a temperature-independent antigen binding antibody from a plurality of antibodies, e.g. for use in a pharmaceutical composition, comprising the step of selecting an antibody with an equilibrium binding constant $K_D$ (M) remaining constant or decreasing with increasing temperature.

In one embodiment of the methods according to the invention the temperature is in the range of from 13° C. to 37° C.

An additional aspect of the invention is a method for the selection of a temperature-independent antigen binding antibody from a plurality of antibodies, e.g. for use in a pharmaceutical composition, comprising the steps of
  i) determining temperature-dependent kinetic data,
  ii) calculating transition state (TS) thermodynamic properties, and
  iii) selecting an antibody based on the thermodynamic behavior.

In one embodiment the methods according to the invention are characterized in that said thermodynamic behavior is a temperature-dependent acceleration of the antigen complex association rate constant $k_a$ [1/Ms] and a remaining or decreasing antigen complex dissociation rate constant $k_d$ [1/s]. In a further embodiment said thermodynamic behavior is an enthalpy-driven $\Delta H^{\circ}\ddagger$ass antigen complex association phase and a binding entropy $\Delta S^{\circ}\ddagger$ass of less than 10 J/K*mol. In another embodiment an antibody is selected with a dissociation phase showing a negative or nearby zero dissociation activation energy (Eadiss [kJ/mol]), a negative dissociation enthalpy ($\Delta H^{\circ}\ddagger$diss [kJ/mol]), and a large negative dissociation entropy ($\Delta S^{\circ}\ddagger$diss [kJ/mol]).

In still a further embodiment the determining of temperature-dependent kinetic data is by surface plasmon resonance and comprises a kinetic screening step and a thermodynamic screening step. In one embodiment said kinetic screening step comprises the calculation of an antigen-complex-stability according to formula (I)

$$\text{antigen-complex-stability} = (1 - [BL(RU) - SL(RU)/BL(RU)]) \quad (I)$$

based on a surface plasmon resonance determination with BL denoting a Binding Late reference point set shortly before the antigen's injection ends, SL denoting a Stability Late reference point set shortly before the end of the complex dissociation phase. In still a further embodiment the methods comprise the step of optimizing the signal response in the surface plasmon resonance determination based on the molecular weight of the antigen, whereby Rmax is kept constant in the temperature range of the determining.

In a further embodiment the methods according to the invention are characterized in that said determining by surface plasmon resonance comprises the following steps:
a) immobilizing an antibody on a solid support surface by a capture molecule bound to said the solid support surface,
b) providing a solution comprising an antigen,
c) flowing a solution containing a known concentration of the antigen over the solid support surface in order to permit association of the antigen to the immobilized antibody,
d) flowing a solution free from the antigen over the solid support surface in order to permit dissociation of the antigen from the immobilized antibody,
e) monitoring during steps c) and d) the time dependent amount of antigen bound to the solid support surface and collecting binding data, wherein steps c) and d) are repeated at least once with a different concentration of the antigen, and
f) calculating kinetic and/or thermodynamic parameters by fitting the binding data obtained in e) to a predetermined model for the interaction between the antigen and the immobilized antibody based on equations (II) to (XIII).

In one embodiment said immobilizing an antibody is by a species specific antibody capture molecule.

An aspect of the current invention is a pharmaceutical composition comprising an antibody produced with a method according to the invention.

In one embodiment the selection of an antibody in the kinetic screening is performed by selecting an antibody with complex stabilities greater than 95%. In still another embodiment the antigen signal response is optimized based on the molecular weight of the antigen.

Another aspect of the current invention is a method for the selection of an antibody by surface plasmon resonance wherein temperature-dependent kinetic data is generated in order to calculate Transition State (TS) thermodynamic properties and an antibody is selected based on the thermodynamic behavior, whereby said generation of temperature-dependent kinetic data is based on a surface plasmon resonance determination and calculation of thermodynamic properties of said antibody with a thermodynamic screening performed at 17° C. with 107 nM, at 21° C. with 78 nM, at 25° C. with 70 nM, at 29° C. with 64 nM, at 33° C. with 58 nM and at 37° C. with 53 nM antibody concentration.

DETAILED DESCRIPTION OF THE INVENTION

The current invention reports methods for the selection of an antibody binding to an antigen, characterized in that temperature-dependent kinetic data is generated in order to calculate Transition State (TS) thermodynamic properties and an antibody is selected based on the thermodynamic behavior It has been found that surface plasmon resonance based kinetic methods have several advantages over conventional calorimetric assays:
high throughput processing is possible,
low sample consumption,
measurement of affinity instead of avidity, and
use of crude cell supernatants or complex cultivation mixtures.

The surface plasmon biosensor surface is an affinity matrix, which is used for example for antibody capturing from cell cultivation supernatants. Thus, crude and complex mixtures can be used as samples. As one of the interacting partners is immobilized on the sensor's surface and the second compound is injected into the flow system, the measurement of equilibrium and transition state thermodynamics is possible, because the FIA (Flow Injection Analysis) system can separately monitor the complex association and dissociation phase. With this technology the calculation of the thermodynamic parameters
free standard binding enthalpy $\Delta G°$,
standard binding enthalpy $\Delta H°$,
standard binding entropy $\Delta S°$,
and of the transition state parameters
free standard association enthalpy $\Delta G°\ddagger ass$,
standard association enthalpy $\Delta H°\ddagger ass$,
standard association entropy $\Delta S°\ddagger ass$,
activation energy Eaass,
free standard dissociation energy $\Delta G°\ddagger diss$,
standard dissociation enthalpy $\Delta H°\ddagger diss$,
standard dissociation entropy $\Delta S°\ddagger diss$, and
dissociation energy Eadiss
is possible. In case of using the non-linear van't Hoff equation a $\Delta C_p$ value is determined.

One aspect of the current invention is a method for the selection of antibodies based on their thermodynamic characteristics.

Generally an SPR-based kinetic antibody screening (see e.g. Steukers, M., et al., J. Immunol. Methods 310(1-2) (2006) 126-35; Rich, R. L., et al., Anal. Biochem. 361(1) (2007) 1-6) is succeeded by a second step of higher resolution thermodynamic SPR analyses.

With a method according to the invention antibodies can be selected, which have an at least constant or increasing affinity at elevated temperatures, i.e. an at least constant or increasing antigen complex stability at elevated temperatures. The antigen complex stability is a major selection criterion in the antibody screening process. Solely primary cell cultures, which produce antibodies with highly stable antigen complexes at 25° C. or 37° C., respectively, are selected.

Antibody producing cell cultures are produced and subjected to, in one embodiment high throughput, analyses, in which the temperature-dependent kinetic data is generated in order to calculate transition state (TS) thermodynamic properties. The selection of the antibody according to the method of the invention is done based on its thermodynamic behavior.

In one embodiment of this aspect the antibody selected is characterized by a temperature-dependent acceleration of the antigen complex association rate constant $k_a$ [1/Ms] and a remaining or decelerated antigen complex dissociation rate constant $k_d$ [1/s]. Such an antibody is typically characterized by an enthalpy-driven $\Delta H°\ddagger ass$ antigen complex association phase and a negative binding entropy $\Delta S°\ddagger ass$, which denotes in this application an "entropic burden". An antibody selected with the method according to the invention is characterized by an antigen interaction mechanism, which shows a large entropy-change in the binding equilibrium. This entropic contribution comes from the antibody-antigen complex dissociation step, wherein a large positive or a large negative change of the dissociation entropy ΔS°‡diss takes place. Moreover, an antibody selected with the method according to the invention may have a thermodynamic anomaly originating from the antigen dissociation phase, where the dissociation rate constant $k_d$ [1/s] surprisingly and unexpectedly decreases with increasing temperature. Such an antibody is characterized by thermodynamic parameters such as i) a dissociation phase showing a negative or nearby zero dissociation activation energy Eadiss [kJ/mol], ii) a negative dissociation enthalpy ΔH°‡diss [kJ/mol], and iii) a large negative dissociation entropy ΔS°‡diss [kJ/mol]. It has to be pointed out that this is a completely theoretical treatment of this effect.

Thus, a method according to the invention allows for the selection of an antibody from a multitude of high affinity antibodies, based on thermodynamic parameters, which provide a basis for the mode of interaction of the selected antibody with the antigen, i.e. that the antibody induces a conformational change in the antigen or that the antibody undergoes a conformational change in itself. Thus, the method is useful for the selection of cells producing antibodies with high antigen complex stability.

In one embodiment comprises the method according to the invention a kinetic screening step and a thermodynamic screening step. For the kinetic screening a Binding Late (BL) reference point is set shortly before the antigen's injection ends and a Stability Late (SL) reference point is set shortly before the end of the complex dissociation phase. In one embodiment is the BL and SL data graphically visualized by an X-Y-plot with the X-axis showing the value in response units (RU) of the Binding Late reference point and the Y-axis showing the value for the Stability Late reference point in RU (for an exemplary plot see FIG. 1). Additionally the antigen-complex-stability can be calculated according to formula (I) based on the BL and SL data:

$$\text{antigen-complex-stability} = (1 - [BL(RU) - SL(RU)/BL(RU)]) \quad (I).$$

In another embodiment is the BL and antigen-complex-stability data graphically visualized by an X-Y-plot with the X-axis showing the value in response units (RU) of the Binding Late reference point and the Y-axis showing the value in percentage for the complex stability (for an exemplary plot see FIG. 2). In one embodiment is the kinetic screening step performed at 25° C. In another embodiment is the kinetic screening performed at 37° C. In another embodiment is the kinetic screening performed at a set of two or more different temperatures between 13° C. and 42° C.

Prior to the thermodynamic screening the single cell deposited clones are cultivated in one embodiment in 100 ml spinner culture flasks using RPMI 1640 medium. In another embodiment the antibodies are purified from the supernatant by Protein A Sepharose™ column chromatography prior to the thermodynamic screening. In one embodiment the system buffer is HBS-EP for the thermodynamic screening. In another embodiment is the sample buffer supplemented with 1 mg/ml carboxymethyldextrane to reduce unspecific sensor matrix effects.

The method according to the invention will be described in the following using as an example the analysis of anti-human PTH antibodies. This examples has not to be interpreted as a limitation of the method according to the invention it is in fact presented in order to exemplify the teaching of the method according to the invention. The scope of the current application is set forth in the claims.

In a first step a kinetic screening of hybridoma supernatants was performed. The Binding Late data and the Stability Late data from 549 hybridoma primary cultures from several immunization and fusion campaigns are illustrated in FIG. 1. Hybridoma cells with sufficient antigen response (BL) and slow antigen complex dissociation (SL) were selected for further screening steps. For example, cells numbered 123, 119, 499, 133, and 295 were used for subsequent processing (see circle in FIG. 1) and cells numbered 189, 263, and 341 were rejected due to insufficient complex stability (see frame in FIG. 1).

To facilitate the identification of antibodies with high antigen response and high complex stability a diagram in which the resulting complex stability in [%] was plotted over the binding late response signal can be used (see e.g. FIG. 2). In one embodiment for the selection of antibodies in the kinetic screening high antigen complex stability binders with complex stabilities 95% or more were selected.

Most publications using SPR-based measurements don't use antibody capture systems as sensor surface presentation technology. Usually the antibody or fragments thereof are covalently immobilized on the sensor. This technology can't be used in a high throughput format, since the surface is not suitable for multi purpose antibody presentation, but it is technically limited by the number of sensors being immobilized with ligands.

If using a capture system for thermodynamic measurements the antibody capture level varies due to the temperature sensitivity of the kinetics (see FIG. 15). To use an antibody capture system for thermodynamics it is absolutely necessary to guarantee a homogeneous, temperature-independent antibody capture level.

There are two main issues for thermodynamic measurements at low temperatures. First, the kinetics of the antibody capture systems are too slow to capture enough secondary antibody for the analysis at lowered temperatures. Second, the kinetics of the antigen-antibody interactions slows down, too. Kinetics shows a strong loss in the assay resolution due to slow kinetics at 4° C. and 11° C. No equilibrium can be achieved in the complete temperature-range. The $R_{max}$ values are small and inhomogeneous in the temperature gradient. With increasing temperature the amount of captured mAb constantly increases due to a faster association rate of the secondary antibody. The antigen kinetics accelerates, too, and the antigen $R_{max}$ values increase with increasing temperature. Since no equilibriums achieved these estimated $R_{max}$ values are rather error-prone. The inhomogeneous sensor performance is responsible for high errors of the thermodynamic calculations. No 95% significance of the calculated parameters can be achieved.

Therefore, the temperature gradient used in the experiment as well as the preparation of the sensor surface need to be optimized. It has been found that the sensor performance is to be optimized primarily by a temperature-dependent titration of the antibody capture system and using an optimized temperature gradient and adapted injection times, so that in the complete run the $R_{max}$ value is constant. The outcome is compared in FIG. 15. $R_{max}$ average is 35 RU+/−3 RU. The equilibrium was achieved at temperatures >30° C. The lowest temperature used here is 15° C. Table 1 compares the thermodynamic parameter calculation for the equilibrium (linear Van't Hoff), the association phase (Eyring and Arrhenius) and dissociation phase (Eyring and Arrhenius), using the conventional versus the optimized assay.

TABLE 1

Thermodynamics of the interactions in the
non optimized and optimized form.

|  | not optimized | | optimized | |
|---|---|---|---|---|
| Parameter Name | Parameter Value | SE | Parameter Value | SE |
| $\Delta H°$ [kJ/mol] | −61 | 9.4 | −59 | 1.2 |
| $\Delta S°$ [J/(K * mol)] | −57 | 32 | −51 | 3.8 |
| $T\Delta S°$ [kJ/mol] | −17 | 9.5 | −15 | 1.1 |
| $\Delta G°$ [kJ/mol] | −44 | 0.13 | −43 | 0.009 |
| $\Delta H°\ddagger$ ass [kJ/mol] | 34 | 7.8 | 37 | 0.64 |
| $\Delta S°\ddagger$ ass [J/(K * mol)] | −49 | 27 | −44 | 2.1 |
| $T\Delta S°\ddagger$ ass. [kJ/mol] | −15 | 8 | −13 | 0.64 |
| $\Delta G°\ddagger$ ass [kJ/mol] | 49 | 0.11 | 50 | 0.005 |
| Ea ass [kJ/mol] | 37 | 7.8 | 39 | 0.64 |
| $\Delta H°\ddagger$ diss [kJ/mol] | 95 | 16 | 95 | 1.8 |
| $\Delta S°\ddagger$ diss. [J/(K * mol)] | 7.5 | 56 | 7.6 | 5.9 |
| $T\Delta S°\ddagger$ diss. [kJ/mol] | 2.2 | 17 | 2.3 | 1.7 |
| $\Delta G°\ddagger$ diss [kJ/mol] | 93 | 0.23 | 93 | 0.014 |
| Ea diss [kJ/mol] | 98 | 16 | 98 | 1.8 |
| van't Hoff | $R^2 = 0.9130$ | | $R^2 = 0.9992$ | |
| Eyring Association | $R^2 = 0.8280$ | | $R^2 = 0.9994$ | |
| Eyring Dissociation | $R^2 = 0.8943$ | | $R^2 = 0.9993$ | |
| Temp range | 4° C.-40° C. | | 15° C.-40° C. | |
| Temp Titration | no | | yes | |
| Association | 2 min | | 3 min | |
| R2 > 95% | no | | yes | |

Data in the row "not optimized" show high errors (SE), whereas the "optimized" data show much lower errors. All $R^2$ values of the "not optimized" assay are below 95% significance, whereas the optimized assay show $R^2 > 95\%$.

The focus is on the $\Delta S°\ddagger$ass values, where the non optimized system shows an error of 55%, whereas the optimized assay shows an error of just 5%.

The appropriate temperature range, association time and titration of the capture kinetics ("Temp. titration") are key parameters to successfully realize thermodynamic measurements in high throughput format. These parameters were optimized in order to measure SPR-based antibody antigen interactions with amenable errors.

In order to perform a thermodynamic screening a species specific capture system with appropriate temperature-dependent secondary antibody complex stability had to be established. Therefore the biosensor was calibrated by using an optimization procedure, which is a second aspect of the current invention. With this procedure it was possible to determine the binding characteristics of murine anti-PTH IgG antibodies with varying epitope specificities in a high throughput format. The thermodynamic screening provides a temperature-dependent set of data (see FIG. 3). At lower temperatures less response was observed, since the capture system's association rate is reduced (see Example 5, Table 2). At higher temperatures the association rate accelerates, so that in one embodiment the concentration and/or the injection time of the antibody in question had to be reduced in order not to capture too much antibody. In one embodiment the antigen signal response is optimized based on the molecular weight of the antigen. For example depending on the PTH molecular weight (9.4 kDa) the antigen signal response at $R_{max}$ was optimized and did not exceed 25 RU.

Therefore, in one embodiment of the method for the selection of antibodies based on the thermodynamic properties a thermodynamic screening step is performed at 17° C. with 107 nM, at 21° C. with 78 nM, at 25° C. with 70 nM, at 29° C. with 64 nM, at 33° C. with 58 nM and at 37° C. with 53 nM (secondary) antibody concentration. For anti-PTH antibodies the hybridoma supernatants were used to capture a constant antibody response level of 320 RU on the sensor surface, whereby 320 RU antibody captured the full length 9.4 kDa PTH analyte at 20 RU at $R_{max}$. In another embodiment of the method according to the invention the $R_{max}$ value is kept constant in the temperature range of from 13° C. to 37° C. by an optimization of the antibody concentration in the solutions applied to the surface plasmon resonance chip based on the weight of the antigen.

It has been found that in order to calculate thermodynamic parameters it is essential to determine the temperature dependent $K_D$ as precise as possible. Also has surprisingly been found that the error of the calculated thermodynamic parameters can be dramatically reduced when analyte-ligand saturation during the complex association is achieved in order to calculate a global, i.e. constant, $R_{max}$ value for the $K_D$ evaluation according to the Langmuir model. Further has it been found that at temperatures below 13° C. the capture system's association kinetics are too slow for a sufficient antibody response. Below 13° C. and above 37° C., the antibody's antigen binding kinetics determination provides for non-linearizable data according to the van't Hoff, Eyring and Arrhenius equations.

In one embodiment the thermodynamic screening is performed at a temperature between 13° C. or 17° C. and 37° C. It has been found that in this temperature range a simple calculation of the thermodynamic equilibrium data according to the linear form of the van't Hoff equation and a simple calculation of transition state thermodynamics according to the linear Eyring and linear Arrhenius equations is possible (Wear, M. A., et al., Anal. Biochem. 359(2) (2006) 285-7; see also FIG. 5). In one embodiment all measurements are performed under the same conditions in order to make high-throughput-screening (HTS) amenable.

For the calculation the following formulas have been used for a) van't Hoff calculations:

$$\Delta G° = \Delta H° - T^*\Delta S° \quad (II)$$

$$\Delta G° = -R^*T^*\ln K_D \quad (III)$$

$$\ln K_D = -1/T^*(\Delta H°/R)/\text{slope} - (\Delta S°/R)/\text{intercept} \quad (IV)$$

$$R^*T^*\ln K_D = \Delta H°_{T0} - T^*\Delta S°_{T0} + \Delta C°_p(T-T_0) - T^*\Delta C°_p \ln(T/T_0) \quad (V)$$

b) Eyring association phase:

$$k_a = (k_b^*T/h)^*e^{(-\Delta G°\ddagger/R^*T)} \quad (VI)$$

$$\ln k_a/T = -1/T^*(\Delta H°\ddagger/R)/\text{slope} + (\Delta S°\ddagger/R + \ln k_b/h)/\text{intercept} \quad (VII)$$

$$k_a = A^*e^{-Ea/R^*T} \quad (VIII)$$

$$\ln k_a = \ln A/\text{intercept} - (1/T^*Ea/R)/\text{slope} \quad (IX)$$

c) Eyring dissociation phase:

$$k_d = (k_b^*T/h)^*e^{(-\Delta G°\ddagger/R^*T)} \quad (X)$$

$$\ln k_d/T = -1/T^*(\Delta H°\ddagger/R)/\text{slope} + (\Delta S°\ddagger/R + \ln k_B/h)/\text{intercept} \quad (XI)$$

$$k_d = A^*e^{-Ea/R^*T} \quad (XII)$$

$$\ln k_d = \ln A/\text{intercept} - (1/T^*Ea/R)/\text{slope} \quad (XIII)$$

with

---
ΔH° - standard binding enthalpy,
ΔS° - standard binding entropy,
ΔG° - free standard binding enthalpy,
T*ΔS° - entropic term,
ΔH°‡ass - standard association binding enthalpy,
ΔS°‡ass - standard association binding entropy,
ΔG°‡ass - standard association free binding enthalpy,
Ea ass - Arrhenius Parameter for the association,
ΔH°‡diss - standard dissociation binding enthalpy,
ΔS°‡diss - standard dissociation binding entropy,
ΔG°‡diss - standard dissociation free binding enthalpy,
Eadiss - Arrhenius Parameter for the dissociation,
$k_D$ - affinity constant,
$k_a$ - association rate constant,
$k_b$ - Boltzmann Constant = $(1.3806503 \times 10^{-23} \, m^2 \, kg \, s^{-2} \, K^{-1})$,
$k_d$ - dissociation rate constant,
h - Planck constant,
$C_p$ - molar heat capacity.

---

It has surprisingly been found that using a temperature range symmetrically around 25° C. and in steps of +4° C. (as in one embodiment in steps of 13° C., 17° C., 21° C., 25° C., 29° C., 33° C., 37° C.) it is possible to reduce the absolute error of ΔH°, ΔH°‡ass, ΔH°‡diss and ΔS°, ΔS°‡ass, ΔS°‡diss (Zhukov, A., et al., J. Mol. Recognit. 20(5) (2007) 379-385). For example values see Table 2.

TABLE 2

Exemplary thermodynamic parameters of the two anti-PTH antibodies M 9.10.20 and M 1F8.

| Parameter | Antibody 9.10.20 Value | SE | 1F8 Value | SE |
|---|---|---|---|---|
| ΔH° [kJ/mol] | −100 | 9.3 | 53 | 1.3 |
| ΔS° [J/(K * mol)] | −180 | 31 | 350 | 4.3 |
| TΔS° [kJ/mol] | −53 | 9.3 | 100 | 1.3 |
| ΔG° [kJ/mol] | −51 | 0.032 | −51 | 0.0081 |
| ΔH°‡ ass. [kJ/mol] | 45 | 0.39 | 33 | 1.2 |
| ΔS°‡ ass. [J/(K * mol)] | −14 | 1.3 | −35 | 4.1 |
| TΔS°‡ ass. [kJ/mol] | −4.3 | 0.39 | −11 | 1.2 |
| ΔG°‡ ass. [kJ/mol] | 49 | 0.0013 | 43 | 0.0078 |
| Ea ass. [kJ/mol] | 47 | 0.39 | 35 | 1.2 |
| ΔH°‡ diss. [kJ/mol] | 150 | 9.1 | −20 | 2.2 |
| ΔS°‡ diss. [J/(K * mol)] | 160 | 30 | −380 | 7.4 |
| TΔS°‡ diss. [kJ/mol] | 49 | 9.1 | −110 | 2.2 |
| ΔG°‡ diss. [kJ/mol] | 100 | 0.031 | −94 | 0.014 |
| Ea diss. [kJ/mol] | 150 | 9.1 | −18 | 2.2 |

The temperature dependency of the free binding enthalpy ΔG° is calculated for each temperature in the range from 13° C. to 37° C. with the formula $\Delta G° = -R*T*\ln K_D$. If the value is constant the linear form of the van't Hoff equation is used. If ΔG° changes the non-linear form is preferred.

Different characteristics of different anti-PTH antibodies can be seen from the diagrams and are explained in the following paragraphs:

a) The anti-PTH antibody M D1.1 as depicted in FIG. 4 *a*) shows a high affinity and a typical temperature-induced affinity-decrease ($K_D$) from a sub-nanomolar affinity at 17° C. to a nanomolar affinity at 37° C. This is primarily due to a decreasing antigen complex stability at elevated temperature. The dissociation rate covers a two orders of magnitude decrease in complex stability. The association rate constant and the dissociation rate constant both increase, i.e. association and also dissociation are accelerated, resulting in an overall lower binding affinity. In FIG. 7 *a*) the association rate constant $k_a$ [1/Ms], the dissociation rate constant $k_d$ [1/s] and the temperature [° C.] of the anti-PTH antibody M D1.1 is plotted. The antibody performs thermodynamically regular. The association rate constant and the dissociation rate constant both accelerate with increasing temperature. The affinity is calculated as the quotient of $k_d/k_a=K_D$. The result is an exponentially decreasing affinity $K_D$ [M]. The slope of the graph becomes negative. This antibody would not be selected with the method according to the invention.

b) The anti-PTH antibody M 9.3.1 as depicted in FIG. 4 *b*) shows a slight affinity-decrease ($K_D$) with increasing temperature, which remains in the same order of magnitude. The association rate constant $k_a$ increases, so that the strongly accelerated dissociation rate constant $k_d$ can't affect the affinity $K_D$ to much. The antibody M 9.3.1 has a sub-nanomolar affinity at the one hand, but it shows a lacking antigen-antibody-complex stability at elevated temperature. This antibody is a typical example for an antibody not selected with the method according to the invention. In FIG. 7 *b*) the association rate constant $k_a$ [1/Ms], the dissociation rate $k_d$ constant [1/s] and the temperature [° C.] for the antibody M 9.3.1 is shown. The antibody performs thermodynamically regular, which means, that the association rate constant and the dissociation rate constant are both accelerating with increasing temperature. The affinity is calculated as the quotient of $k_d/k_a=K_D$. The result is an exponentially decreasing affinity $K_D$ [M]. This antibody would not be selected with the method according to the invention.

c) The anti-PTH antibody M 9.10.20 as depicted in FIG. 6 *a*) shows an association rate constant $k_a$ acceleration, i.e. an increase of the association rate, with increasing temperature. The association rate constant covers two orders of magnitude whereas the dissociation rate constants stay within 1 order of magnitude. The full range of kinetic power is finally achieved not before 37° C. As the dissociation rate constant $k_d$ just moderately accelerates the antibody M 9.10.20 is an example for an antibody which would be selected with a method according to the invention. The antibody provides high complex stability at 37° C. In FIG. 8 *a*) the association rate constant $k_a$ [1/Ms], the dissociation rate constant $k_d$ [1/s] and the temperature [° C.] of antibody M 9.10.20 is plotted. The antibody performs thermodynamically regular, but the affinity keeps constant in the interval 13° C. to 29° C. and just slightly decreases in the interval 29° C. to 37° C. Although the dissociation rate slightly increases at higher temperatures this antibody nevertheless shows still high antigen complex stability at 37° C. and therefore is a positive screening result obtained with the method according to the invention.

d) The anti-PTH antibody M 1F8 as depicted in FIG. 6 *b*) shows an affinity-increase (decreasing $K_D$) with increasing temperature due to an extremely high antigen-antibody-complex stability ($k_d$) at elevated temperatures. Because the association rate constant $k_a$ increases and the dissociation rate constant $k_d$ decreases, i.e. slows down, an increased affinity at higher temperatures can be determined. The antibody has a $K_D$=1.7 nM at 17° C. and a $K_D$=0.4 nM at 37° C. Because the dissociation rate constant $k_d$ decreases the anti-PTH antibody M 1F8 is an example for a positive screening result of the method according to the invention. This antibody provides highest antigen-antibody-complex stability at 37° C. In FIG. 8 *b*) the association rate constant $k_a$ [1/Ms], the dissociation rate constant $k_d$ [1/s] and the temperature [° C.] of antibody M 1F8 is plotted. This antibody shows a thermodynamic anomaly. The association rate accelerates with increasing temperature, but in contrast to antibodies M 9.3.1, M D1.1 and M 9.10.20 the dissociation rate is reduced with increasing temperature. This results in an affinity increase with increasing temperature. The slope of the curve becomes positive.

This antibody is a typical positive screening result obtained with the method according to the invention.

The data obtained in the thermodynamic screening can be visualized in a double logarithmic plot as depicted in FIG. 9 a) wherein the kinetic rate constants ($k_{on}$) $k_a$ [1/Ms] and ($k_{off}$) $k_d$ [1/s] are denoted on the X- and Y-axis, respectively. Isometric lines (solid lines) indicate areas of the same affinities, which are plotted in bold at the right side of the diagram. Since the quotient of $k_d/k_a$ provides for the equilibrium constant $K_D$ [M], each data point is equivalent to an affinity at a respective temperature. The arrow above symbolizes the temperature gradient in steps of +4° C. starting at 13° C. or 17° C., respectively, and ending at 37° C.

Temperature-dependent affinity trends of each antibody are connected by a line. The temperature-dependent affinity screen shows that from the 34 depicted antibodies only one antibody shows the looked for temperature-dependent behavior (filled black diamonds). Such an antibody will be selected with the method according to the invention. Three exemplary affinity trends are shown in FIG. 9 b). In this rate map the $K_D$s in steps of +4° C. of three example antibodies are shown, whereof one is an antibody with increasing affinity with increasing temperature, one is an antibody with constant affinity with increasing temperature, and one is an antibody with decreasing affinity with increasing temperature. Most antibodies show an affinity loss due to lacking antigen complex stability (like those represented by the square in FIG. 9 b)). The affinity remains constant when $k_{on}$ and $k_{off}$ increase (circles). Thus, in one embodiment of the method according to the invention an antibody is selected that shows an increase in $k_{on}$ and $k_{off}$ with increasing temperature. In one embodiment $k_{on}$ accelerates and $k_{off}$ decelerates, the affinity increases and the complex gains stability at higher temperatures (filled circles). Thus, in one embodiment of the method an antibody is selected that shows an acceleration of $k_{on}$ and a deceleration of $k_{off}$ with increasing temperature in the temperature range of from 17° C. to 37° C. The high throughput screening of temperature stable antibody antigen interactions is the core of the high throughput method described. In one embodiment of the method according to the invention an antibody is selected that has an increasing or a constant affinity for an antigen in the temperature range of from 17° C. to 37° C. In the method according to the invention antibodies like these are selected. In another embodiment of the method according to the invention an antibody is selected that has an increasing affinity in the temperature range from 17° C. to 37° C. Temperature-dependent kinetics is used to select antibodies with enhanced antigen complex stability.

The monitoring of the temperature-dependent kinetics as shown in FIG. 9 is the basis for the selection of antibodies with temperature-independent or temperature-increasing antigen complex stability with the method according to the invention.

As already outlined above antibodies M 9.10.20 and M 1F8 show a temperature-dependent complex stability and would be selected with the method according to the invention. In FIG. 10 a), the affinity ($K_D$) at 37° C. of antibodies is plotted over the affinity at 25° C. Just one antibody thereof (No. 8: anti-PTH antibody M 1F8) shows an increase of its affinity with increasing temperature. The other antibodies' affinities remain constant or decrease. When having a look at FIG. 10 b) it becomes obvious why the affinity index is only one item of the method described. In FIG. 10 b) two of the 13 anti-PTH antibodies show sufficient antigen complex stability (Nr. 8: anti-PTH antibody M 1F8 and Nr. 13: anti-PTH antibody M 9.10.20). These antibodies would be selected with the method according to the invention. Thus, antibody M 9.10.20 would not have been selected by just focusing on the affinity index, since it populates the correlation corridor of the affinity plot at the left side of FIG. 10 a).

In FIG. 5 on the left side, exemplary data plots of the thermodynamic calculations for the anti-PTH antibody M D1.1 are shown. On the right side of FIG. 5 the corresponding equations are shown. The antibody M D1.1 as an example performs in a regular way, which is verified by the negative slopes of all linearizations.

Table 2 shows, that antibody M 9.10.20 is an enthalpic binder having a high binding enthalpy ($\Delta H°=-100$ kJ/mol). The high negative entropy value ($\Delta S°=-180$ J/mol*K) arises in the dissociation phase ($\Delta S°\ddagger diss=160$ J/K*mol). The antibody M 1F8 is driven into equilibrium by entropic forces ($\Delta H°=53$ kJ/mol, $\Delta S°=350$ J/mol*K). Since antibody M 1F8 increases its affinity with increasing temperature the parameters $\Delta H°\ddagger diss$, $\Delta S°\ddagger diss$, and Eadiss turn into negative values (see Table 2, right column, last five rows). In fact, that does mean that the M 1F8/PTH complex must be frozen to get dissociated. This can be seen as a thermodynamic anomaly. Therefore the values for antibody M 1F8 from the dissociation phase implicate a just formal correctness of the corresponding equations. Nevertheless, both antibodies show the same free binding enthalpy ($\Delta G°=-51$ kJ/mol). Despite of the high entropy changes in the equilibrium, both antibodies show an enthalpic association phase and a negative entropic burden (M 9.10.20 $\Delta S°\ddagger ass=-14$ J/K*mol, M 1F8 $\Delta S°\ddagger ass=-35$ J/K*mol). In one embodiment an antibody with an enthalpic association phase and a negative entropic burden is selected. In both cases the rate limiting step of the interaction antibody-antigen is the dissociation phase (M 9.10.20 $\Delta G°\ddagger diss=100$ kJ/mol; M 1F8 $\Delta G°\ddagger diss=94$ kJ/mol). These values are more than double the $\Delta G°\ddagger ass$ values and reflect the kinetic screening and the selection according to antigen complex stability. Therefore, in one embodiment of the method the screening aim is to select antibodies with a $\Delta G°\ddagger diss/\Delta G°\ddagger ass$ ratio of at least 2.3 or higher. In one embodiment of the method according to the invention an antibody is selected with a rate-limiting dissociation phase or with a $\Delta G°\ddagger diss$ of 80 kJ/mol or more.

In FIG. 11 the equilibrium thermodynamic parameters of 12 exemplary anti-PTH antibodies, calculated according to the van't Hoff equation (III) are shown. The antibodies M 1F8 (left) and M 9.10.20 (right) show thermodynamic equilibrium parameters, which make these antibodies to selected antibodies according to the method according to the invention. Among the exemplified antibodies in FIG. 11 the antibodies M 1F8 and M 9.10.20 have high $-T\Delta S°$ values. Antibody M 1F8 shows the highest positive entropic contribution and antibody M 9.10.12 shows the highest negative entropic contribution to the antigen interaction. Thus, in one embodiment of the method according to the invention an antibody is selected with a $-T\Delta S°$ value according to van't Hoff equation (III) of a) $-80$ kJ/mol or less or b) of $+40$ kJ/mol or more. Antibodies carrying the numbers 2-10 of FIG. 11 would not have been selected by the method.

According to the method according to the invention the origin of the entropic contribution must be resolved. This is done by the calculation of the transition state thermodynamic parameters. It has been found that time resolved transition state thermodynamics and thus the origin of thermodynamic driving forces has to be resolved in order to select an antibody with temperature-independent binding properties. This is particularly important in order to assess the risk of potential promiscuitive antigen binding tendencies by the determination of the binding entropy $\Delta S°\ddagger ass$. For example, despite showing an entropy-driven binding equilibrium antibody M 1F8 is characterized by an enthalpy-driven association phase (see FIG. 12 and Table 2). The antibody M 9.10.20 is characterized by an enthalpy-driven association phase, too (see FIG. 12 and Table 2). As already indicated and shown in FIG. 13 both antibodies M 1F8 and M 9.10.20 show a negative entropic burden $\Delta S°\ddagger ass$. It has been found that this entropic burden denotes, that the corresponding antibodies associate with the antigen in an enthalpic, i.e. in a highly specific manner. An enthalpy-driven association phase is characterized by the formation of non-covalent interactions with the antigen, such as H-bonds, ionic interactions, van der Waals interactions, but not due to amino acid side chain movements or intensive reorganization of the molecules' surrounding hydrate layer. A negative entropic burden shows that the conformational degree of freedom of the system is reduced. Upon antigen binding, the immune complex gets more rigid due to structural adjustments or due to an ordered rearrangement of water molecules than it was before the complex formation. This characteristic can be seen in a very low or even absent cross-reactivity of the antibody. Thus, one embodiment of the method according to the current invention is the selection of an antibody with an enthalpy-driven association phase with low or no cross-reactivity. Since the entropic contributions to the binding equilibrium do not arise from the association phases they must descend from the dissociation phase (see FIG. 14). Both antibodies, M 1F8 and M 9.10.20, show a large entropic change $\Delta S°\ddagger diss$ originating from the antigen dissociation phase. Thus, in one embodiment of the method according to the invention an antibody is selected with a large entropy change coming from the dissociation phase. Antibody M 1F8 shows the thermodynamic anomaly, characterized by a negative entropy change $\Delta S°\ddagger diss=-380$ J/K*mol. Antibody M 9.10.20 shows a large positive entropy change $\Delta S°\ddagger diss=+160$ J/K*mol. Thus, in one embodiment of the method according to the invention an antibody is selected with an absolute $\Delta S°\ddagger diss$ value of 100 J/K*mol or more. In one embodiment an antibody is selected with an absolute $\Delta S°\ddagger diss$ value of 150 J/K*mol or more. In one embodiment the absolute $\Delta S°\ddagger diss$ value is in the range from 100 J/K*mol to 1000 J/K*mol. The negative binding entropy $\Delta S°\ddagger ass$, the entropic burden, during the antigen association phase, correlates with a fast complex association rate and a low activation energy Eaass, which is typical for highly evolved mature antibodies (Thorpe, I. F., et al., Proc. Natl. Acad. Sci. USA 104(21) (2007) 8821-6). Thus, in one embodiment an antibody selected according to the method according to the invention is an antibody binding to a conformational epitope.

Thus, it is also possible with the methods according to the invention to select antibodies that have cross-reactivity to different antigens, either of the same antigen of different species, or to closely related antigens, such as IL-1a and IL-1b. Also is it possible to select antibodies that introduce conformational changes in the antigen, which are e.g. useful as catalytic antibodies.

The antibody according to the invention can be produced. Methods for recombinant production of antibodies are known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective light and heavy chains are inserted into expression vectors by standard methods. Expression is performed in appropriate prokaryotic or eukaryotic host cells like CHO cells, NS0 cells, SP2/0 cells, HEK293 cells, COS cells, PER.C6(R) cells, yeast, or *E. coli* cells, and the antibody is recovered from the cells (supernatant or cells after lysis). General methods for recombinant production of antibodies are well-known in the state of the art and described, for example, in the review articles of Makrides, S.C., Protein Expr. Purif. 17 (1999) 183-202; Geisse, S., et al., Protein Expr. Purif. 8 (1996) 271-282; Kaufman, R. J., Mol. Biotechnol. 16 (2000) 151-160; Werner, R. G., Drug Res. 48 (1998) 870-880.

The term "host cell" as used in the current application denotes any kind of cellular system which can be engineered to generate the antibodies according to the current invention. In one embodiment HEK293 cells and CHO cells are used as host cells. As used herein, the expressions "cell," "cell line," and "cell culture" are used interchangeably and all such designations include progeny. Thus, the words "transformants" and "transformed cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A transient expression system (HEK 293) is reported by Schlaeger, E.-J., and Christensen, K., in Cytotechnology 30 (1999) 71-83 and by Schlaeger, E.-J., in J. Immunol. Methods 194 (1996) 191-199.

The following examples and figures are provided to aid the understanding of the present invention, the true scope of which is set forth in the appended claims. It is understood that modifications can be made in the procedures set forth without departing from the spirit of the invention.

b) Exemplary concentration-dependent sensograms of the temperature-dependent antibody-PTH interaction of antibody M 9.3.1. The kinetics were measured in HBS-EP pH 7.4 at 25° C., 3 min. association time, 15 min. dissociation time, fitting according to a Langmuir 1.1. model.

Figure 5:
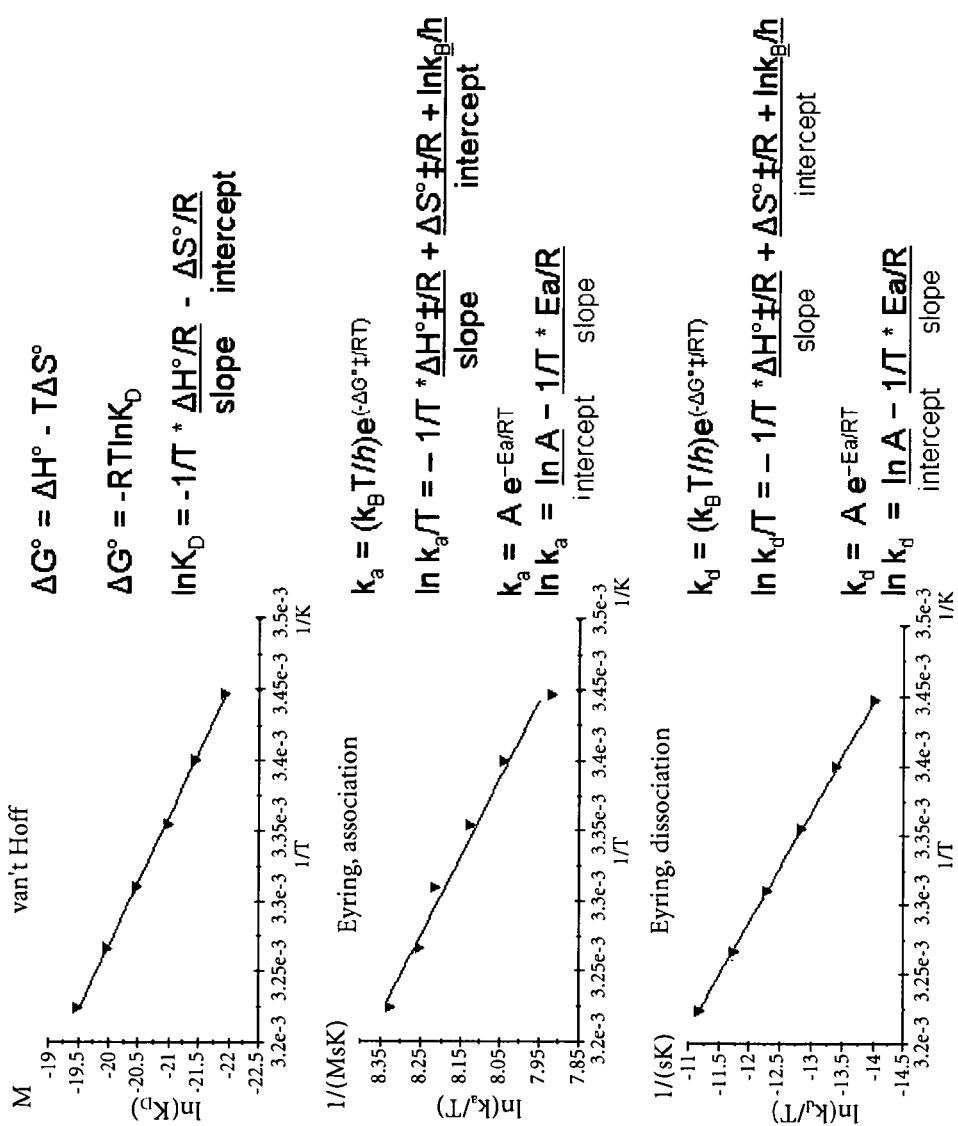

FIG. 5 Calculation of thermodynamic parameters according to the linear equations of van't Hoff, Eyring and Arrhenius. Exemplary plots shown for antibody M D1.1.

Figure 6:
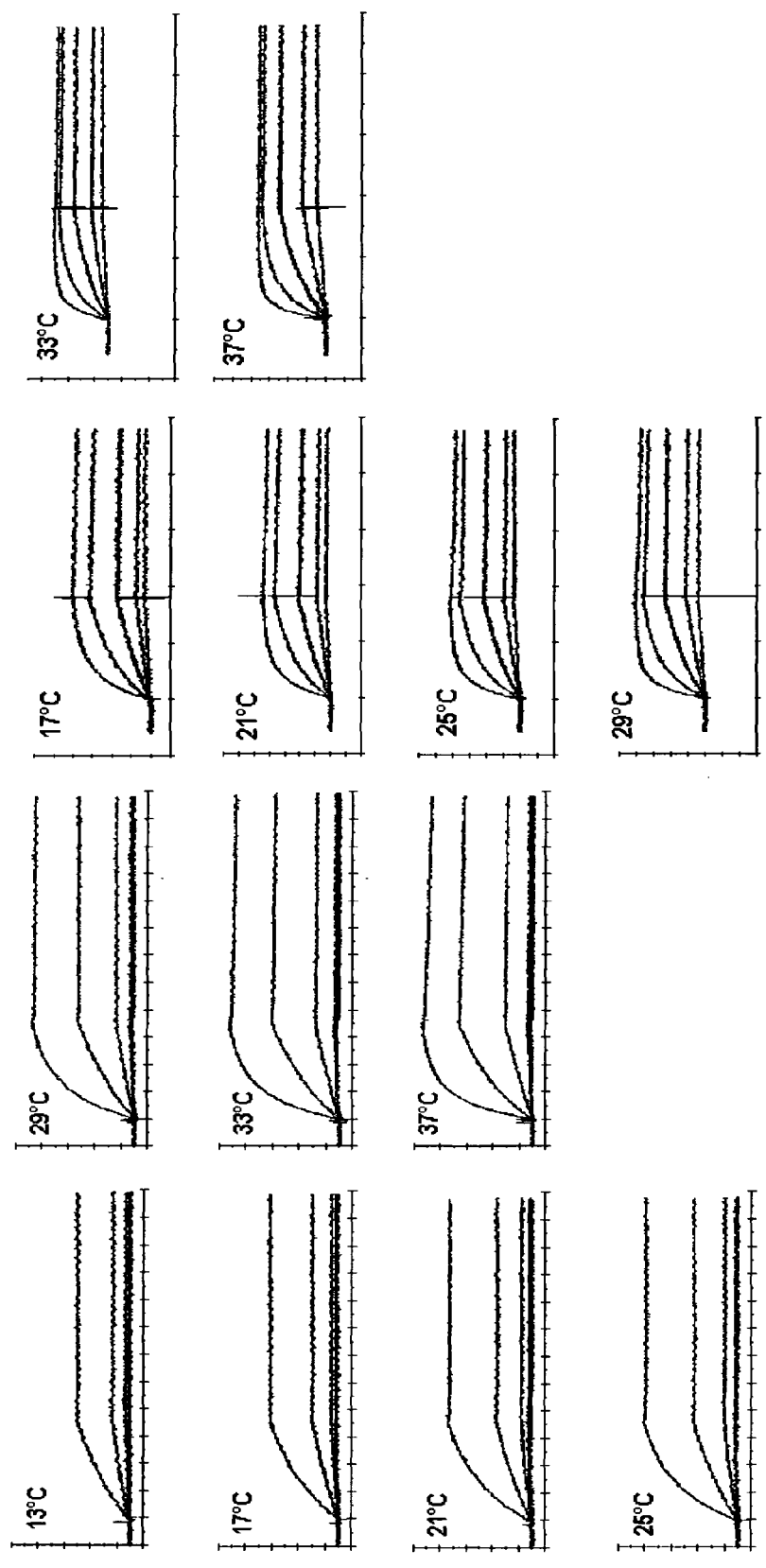

FIG. 6 a) Exemplary concentration-dependent sensograms of the temperature-dependent antibody-PTH interaction of antibody M 9.10.20. The kinetics were measured in HBS-EP pH 7.4 at 25° C., 3 min. association time, 15 min. dissociation time, fitting according to Langmuir;

b) Exemplary concentration-dependent sensograms of the temperature-dependent antibody-PTH interaction of antibody M 1F8. The kinetics were measured in HBS-EP pH 7.4 at 25° C., 3 min. association time, 5 min. dissociation time, fitting according to a Langmuir 1.1. model.

Figure 7:
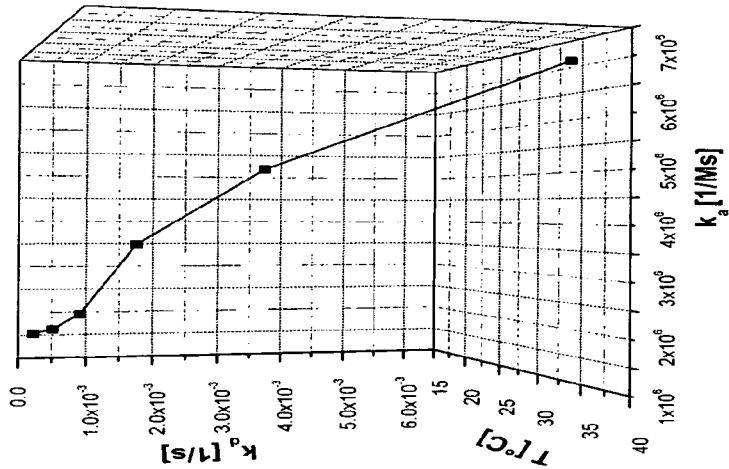
Figure 7:
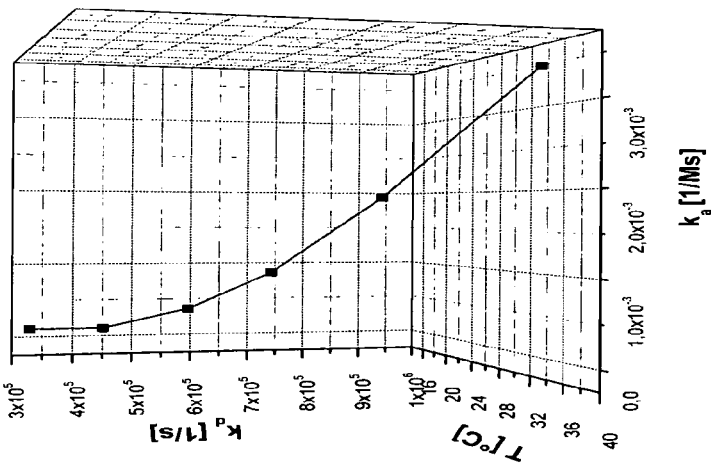

FIG. 7 a) Three dimensional rate map of the data of antibody M D1.1.

b) Three dimensional rate map of the data of antibody M 9.3.1.

Figure 8:
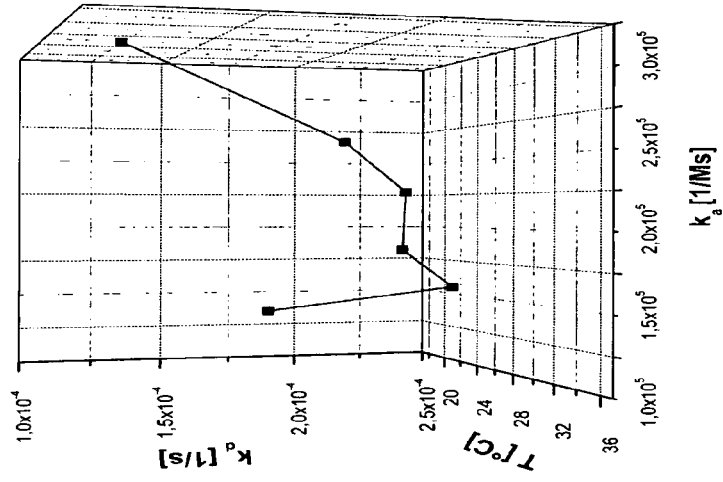
Figure 8:
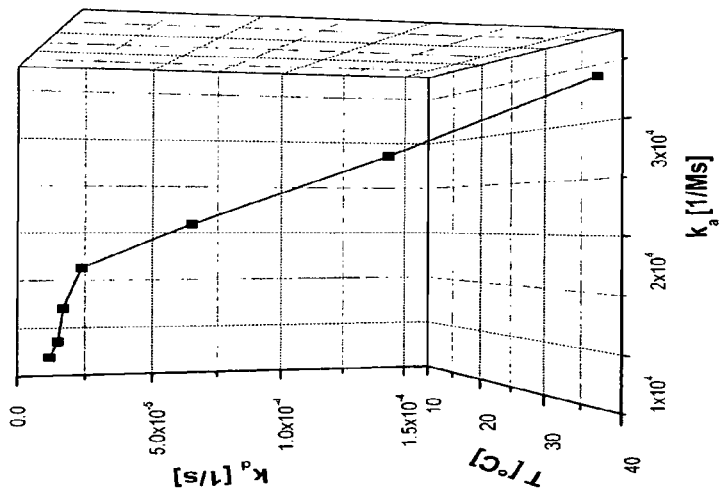

FIG. 8 a) Three dimensional rate map of the data of antibody M 9.10.20;

b) Three dimensional rate map of the data of antibody M 1F8.

Figure 9:
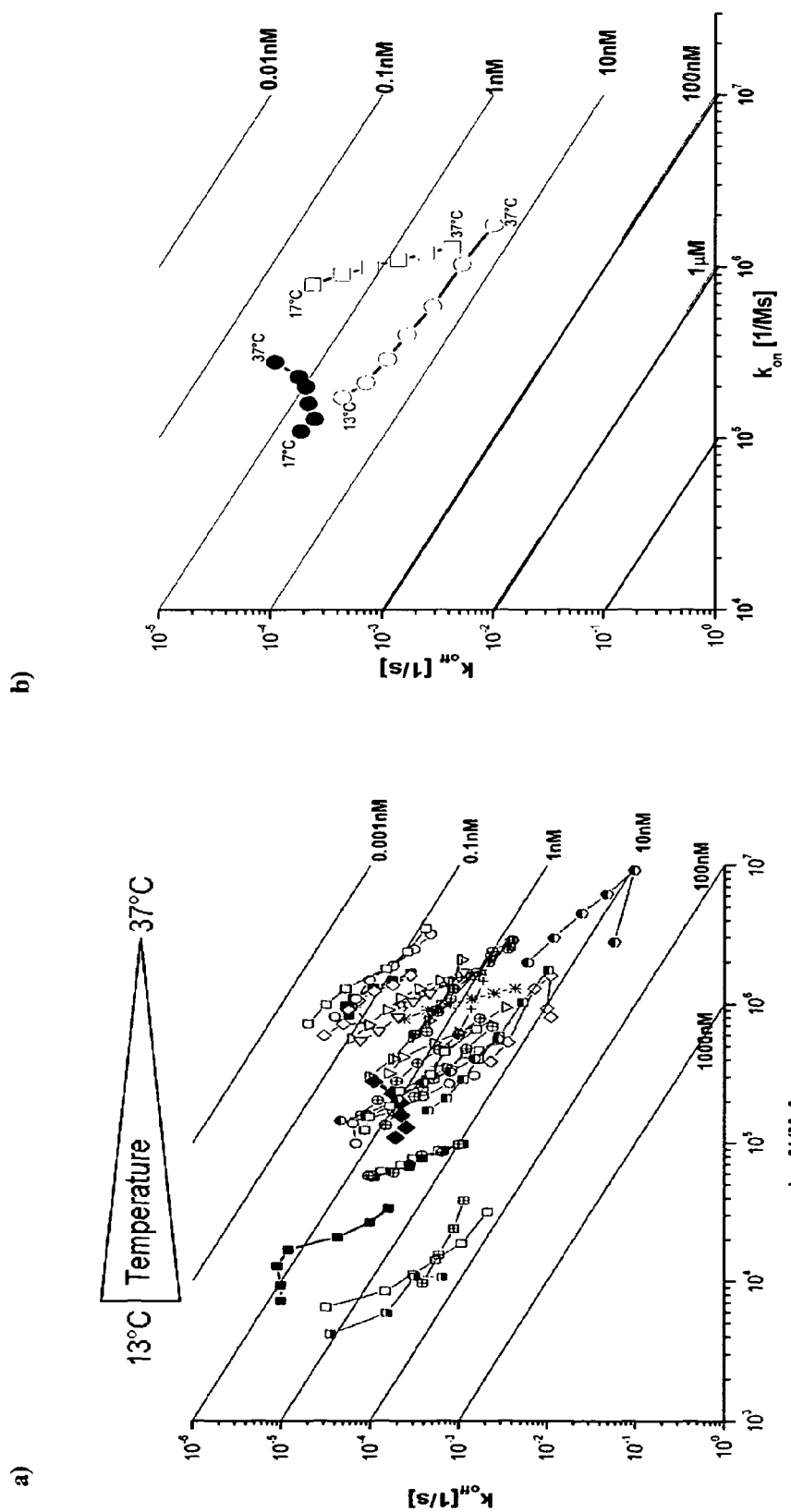

FIG. 9 a) Double logarithmic plot of the temperature-dependent characteristics of 34 exemplary antibodies;

b) Double logarithmic plot of the temperature-dependent characteristics of three exemplary antibodies: filled circles—antibody with increasing affinity with increasing temperature, open circles—antibody with constant affinity with increasing temperature, squares—antibody with decreasing affinity with increasing temperature.

Figure 10:
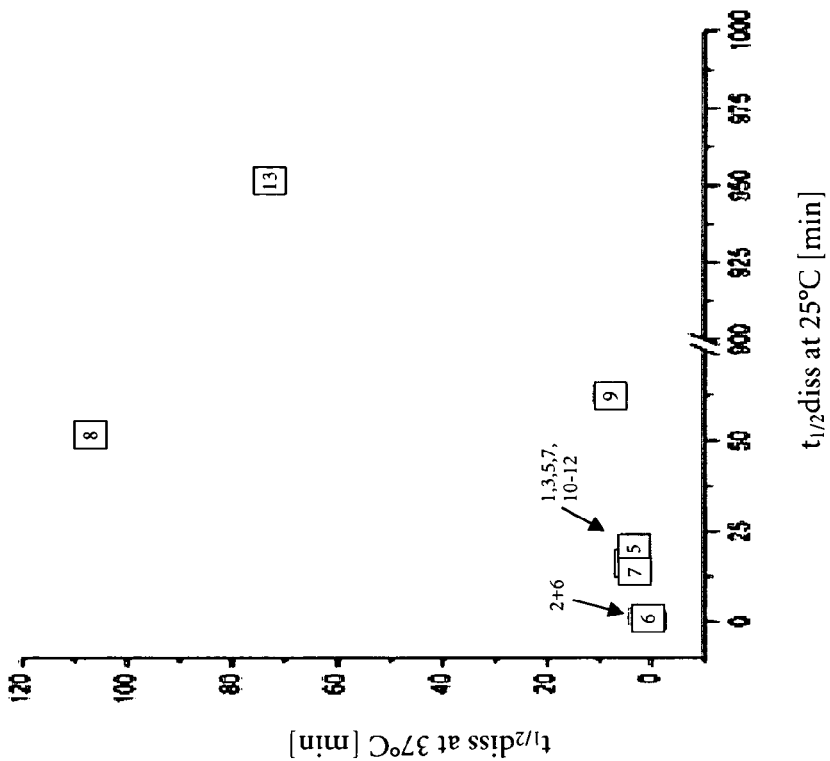
Figure 10:
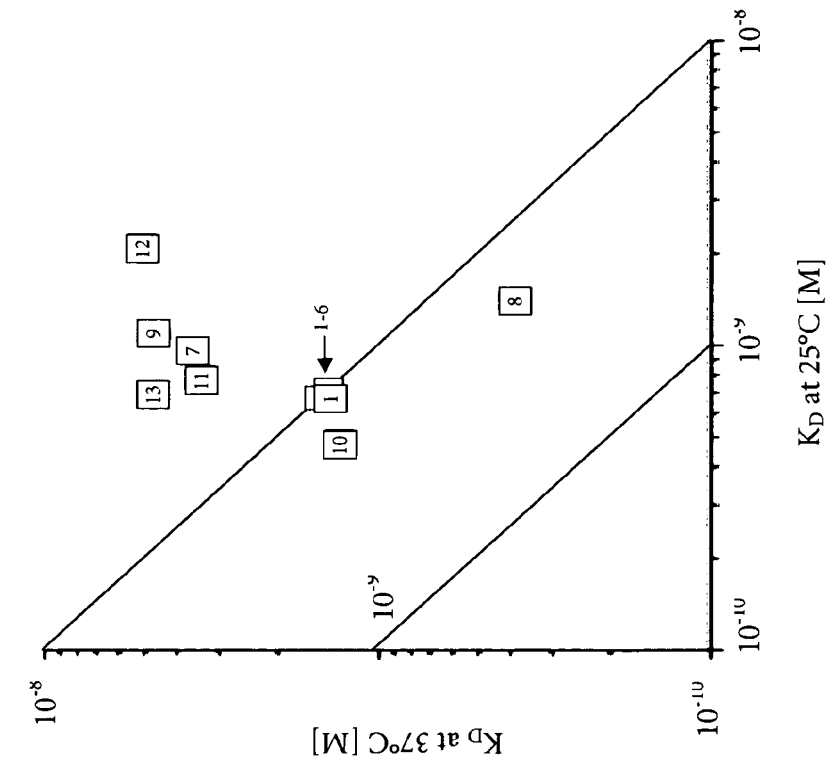

FIG. 10 a) Affinity plot of 13 anti-PTH antibodies from the PTH screening indicating affinities at 25° C. (X-axis) and 37° C. (Y-axis).

b) Dissociation rate constant plot of the same antibodies as in a) at 25° C. (X-axis) and 37° C. (Y-axis).

Figure 11:
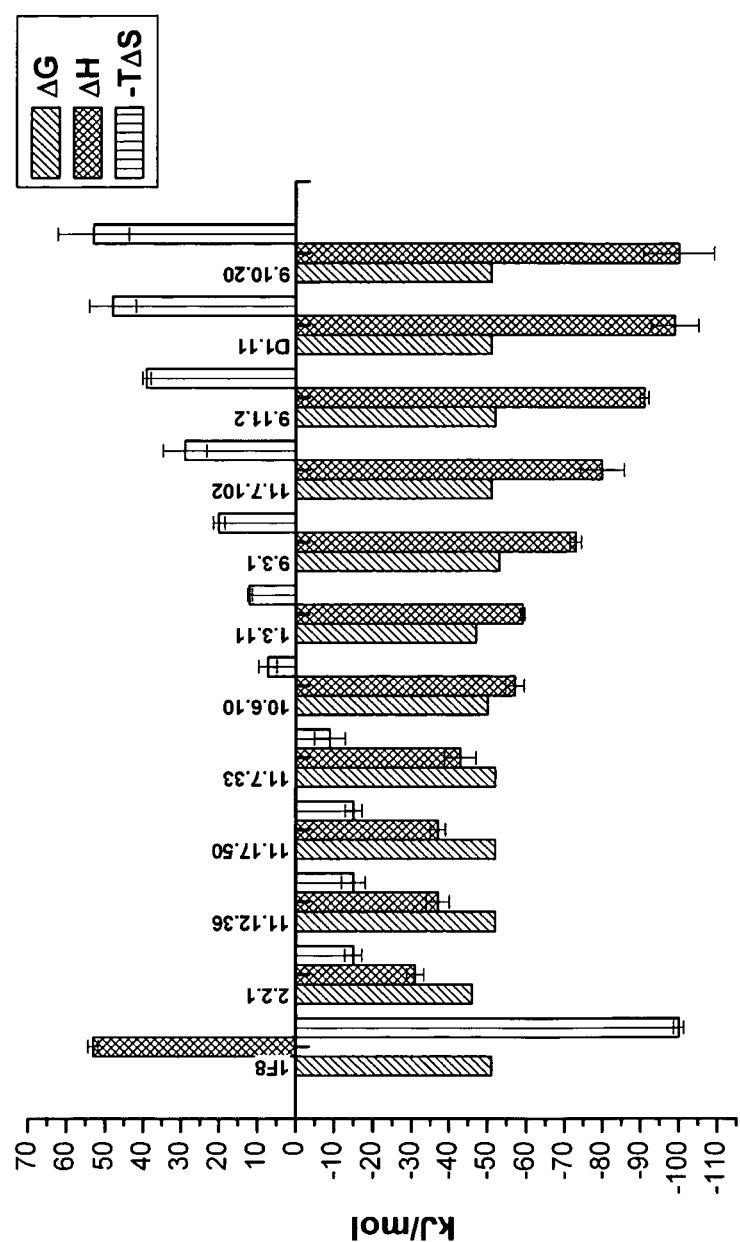
Figure 12:
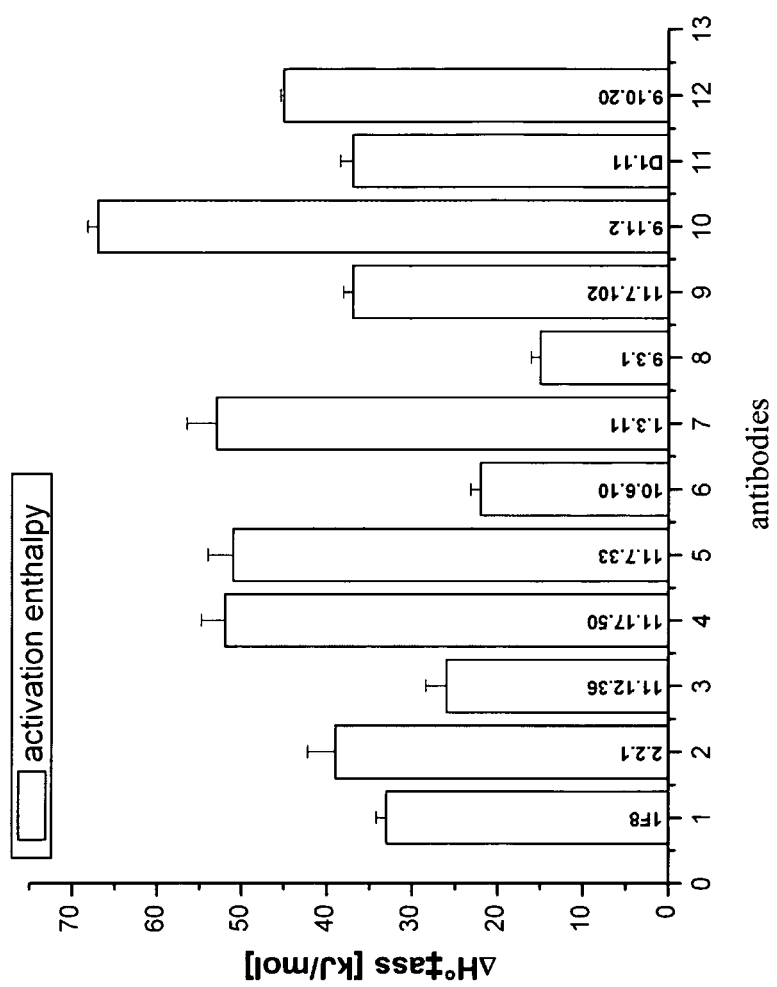

FIG. 11 Equilibrium thermodynamics plot of 12 exemplified anti-PTH antibodies calculated according to van't Hoff FIG. 12 Transition state thermodynamic plot of the activation enthalpies $\Delta H°\ddagger ass$ of 12 exemplified anti-PTH antibodies, calculated according to the Eyring equation.

Figure 13:
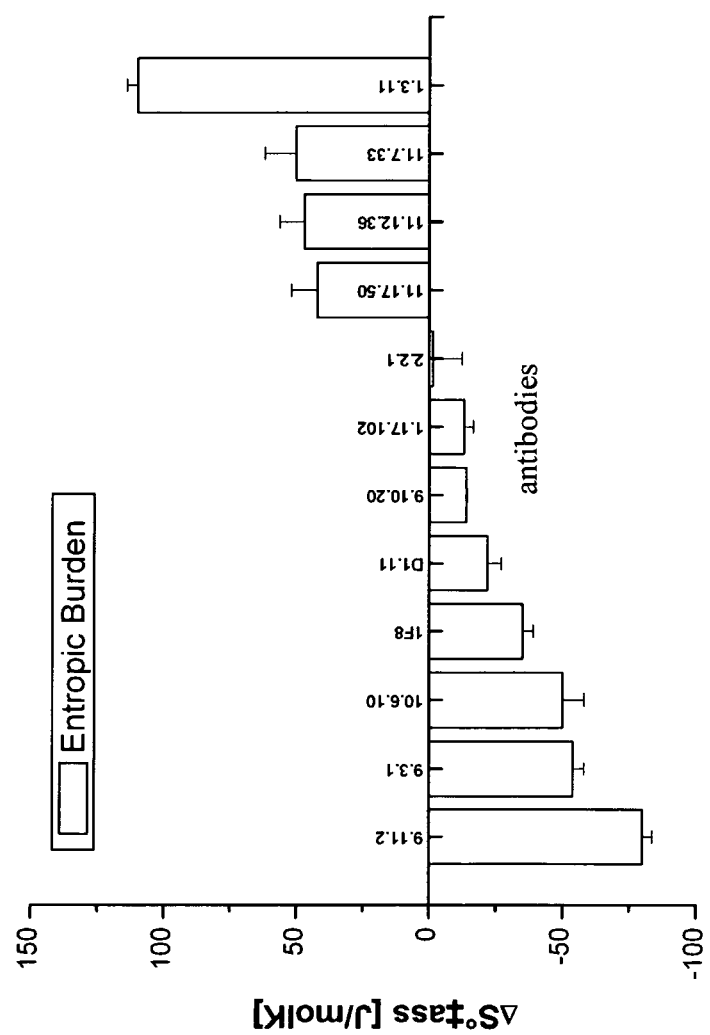

FIG. 13 Transition state thermodynamic plot of the activation entropy $\Delta S°\ddagger ass$ (entropic burden), calculated according to the Eyring equation.

Figure 14:
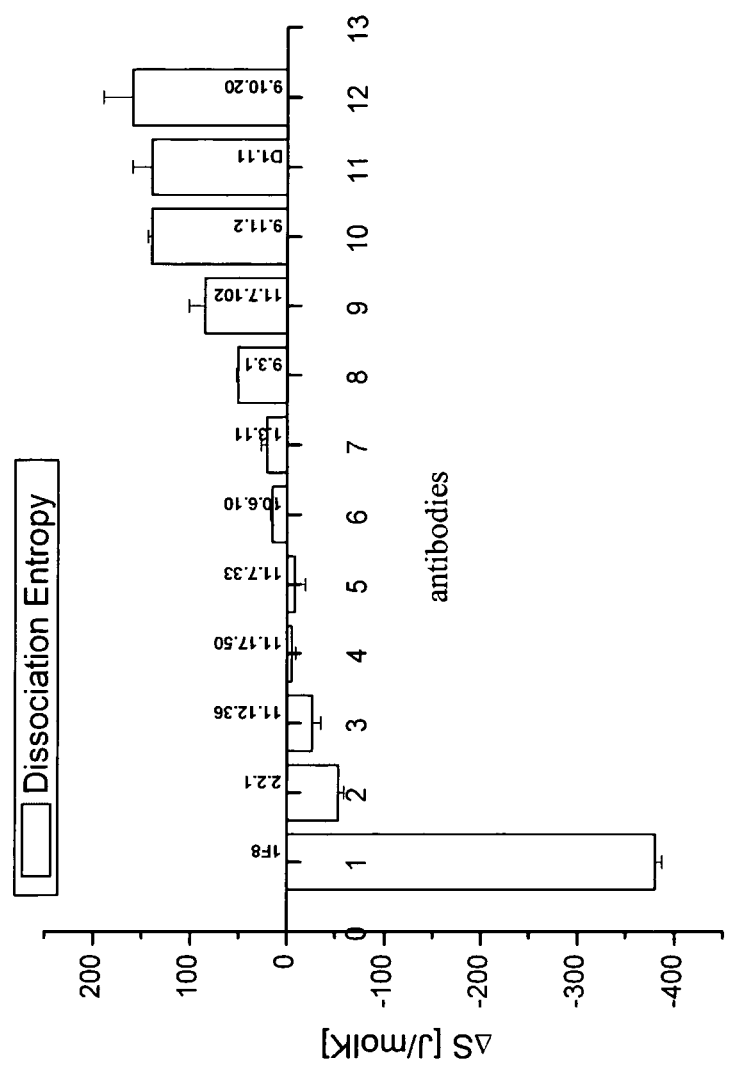

FIG. 14 Transition state thermodynamic plot of the dissociation entropy $\Delta S°\ddagger diss$ of 13 exemplary anti-PTH antibodies, calculated according to the Eyring equation.

Figure 15:
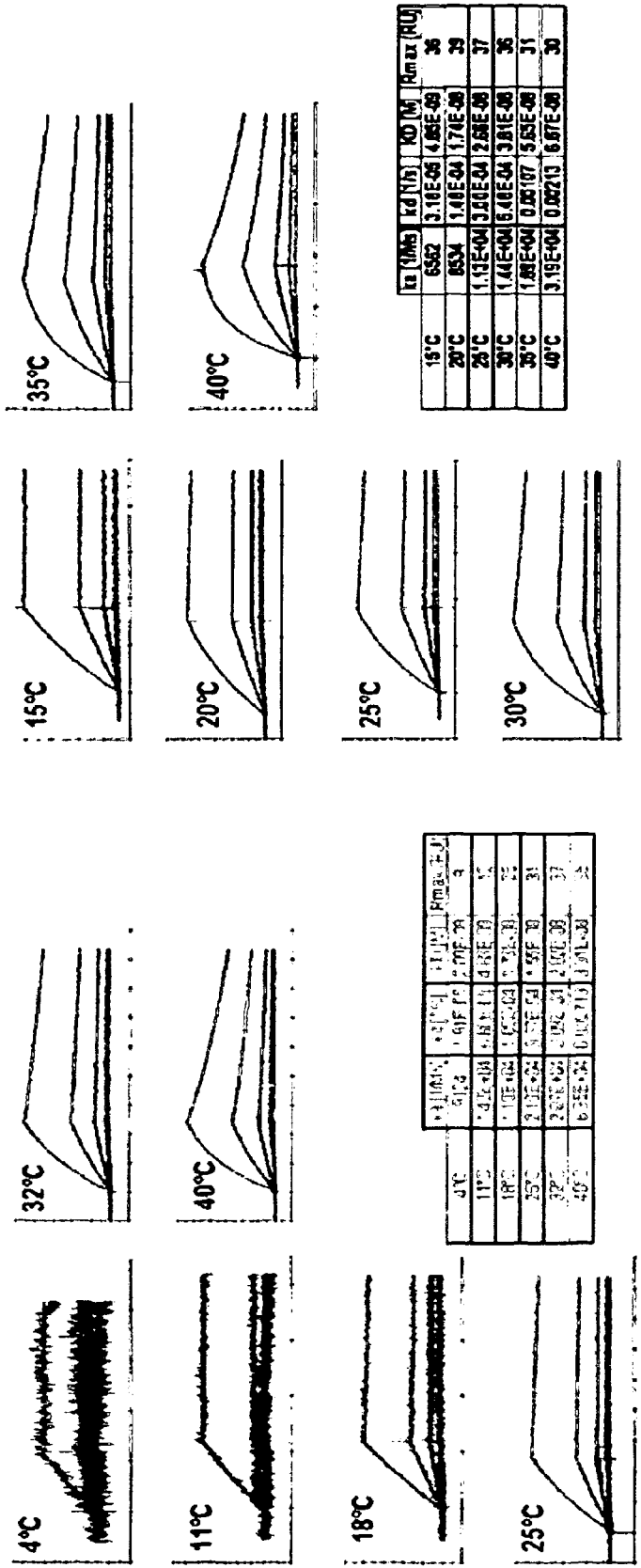

FIG. 15 Temperature- and concentration-dependent measurements of interactions: a) Due to inhomogeneous capture kinetics in the temperature gradient, the $R_{MAX}$ value varies and no equilibrium was achieved at any temperature step during the association phases of the different sensograms; b) Due to an adapted mAb concentration and prolonged association phases the $R_{MAX}$ values are homogeneous, the equilibrium was achieved at temperatures >35° C.

EXAMPLE 1

Immunization of Mice

Balb/c mice 8-12 weeks old were subjected to intraperitoneal immunization with 100 μg human recombinant PTH (Parathyroid hormone) derivatives formulated as a KLH (keyhole limpet haemocyanin) fusion in complete Freud's adjuvant. Recombinant N-terminal and C-terminal PTH fragments as well as full length (1-84) PTH were used as antigens. PTH derivatives were produced synthetically by peptide synthesis.

The immunization was performed 4 times: initial boost, 6 weeks, 10 weeks and 14 weeks after the initial boost. The second and third immunization was done using incomplete Freud's adjuvant. The final boost was done i.v. using 100 μg antigen three days before the hybridoma fusion took place. The production of hybridoma primary cultures was done according to Köhler and Milstein (Kohler, G., et al., Nature 256(5517) (1975) 495-497). The hybridomas were isolated in 96-well micro titer plates (MTPs) by limited dilution and were screened for antigen binding by ELISA methods according to the manufacturer's manual. Primary hybridoma cell cultures, which showed a positive color formation upon antigen binding in ELISA, were transferred into the kinetic screening process.

EXAMPLE 2

Preparation of the CM5 Sensor Chip

The BIAcore A100 system under the control of the Software V.1.1 was prepared like follows: A BIAcore CM5 sensor (series S) was mounted into the system and was hydrodynamically addressed according to the manufacturer's recommendations. A polyclonal rabbit IgG antibody (<IgGFCγM>R, Jackson ImmunoResearch Laboratories Inc., USA) at 30 μg/ml was immobilized at 10,000 RU on spots 1, 2, 4 and 5 in the flow cells 1, 2, 3 and 4 via EDC/NHS chemistry according to the manufacturer's instructions using 10 mM sodium acetate buffer pH 4.5 as pre-concentration buffer. The sensor surface was finally blocked with ethanolamine.

EXAMPLE 3

Kinetic Screening of Primary Hybridoma Culture Supernatants

Hybridoma culture supernatants from different PTH immunization campaigns conducted according to Example 1 were processed as outlined below.

The spots 2 and 4 of a sensor chip obtained according to Example 2 were used as a reference (1-2, 5-4). In order to capture antibody on the sensor surface hybridoma culture supernatants were diluted 1:5 with running buffer HBS-EP (10 mM HEPES pH 7.4, 150 mM NaCl, 1 mM EDTA, 0.05% P20, BIAcore) and were injected at 30 μl/min for 1 min. Subsequently, the respective antigen was injected at 30 μl/min for 2 min. association time. The dissociation phase was monitored for 5 min. Finally the surface was regenerated with a 2 min. injection of 100 mM phosphoric acid.

The sensor was preconditioned by repeated cycles of antibody capturing and regeneration. The monoclonal mouse antibody mAb<TSH>M-1.20 IgG1k (Roche Diagnostics GmbH, Mannheim, Germany) was repeatedly injected for 2 min. at 30 μl/min at 50 nM in HBS-EP and the chip was regenerated using 100 mM $H_3PO_4$ by a 2 min. injection at 30 μl/min.

Figure 1:
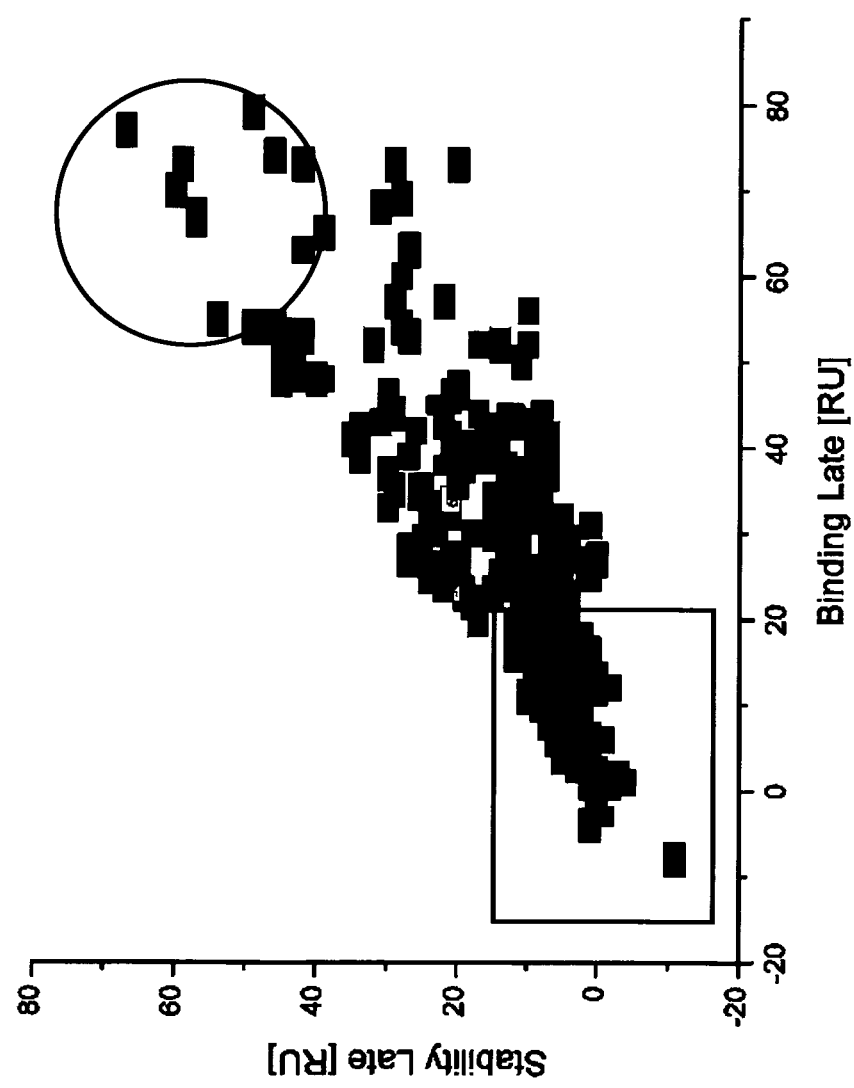
FIG. 1 Illustration of the Binding Late (BL) and Stability Late (SL) data of exemplary anti-PTH antibodies.

For the selection of primary hybridomas the following procedure was used: A Binding Late (BL) reference point was set shortly before the antigen's injection ended. A Stability Late (SL) reference point was set shortly before the end of the complex dissociation phase. The BL and SL data were graphically visualized (FIG. 1). The data was used to calculate the antigen complex stability using formula (I):

$$(1-[BL(RU)-SL(RU)/BL(RU)]) \quad (I)$$

Figure 2:
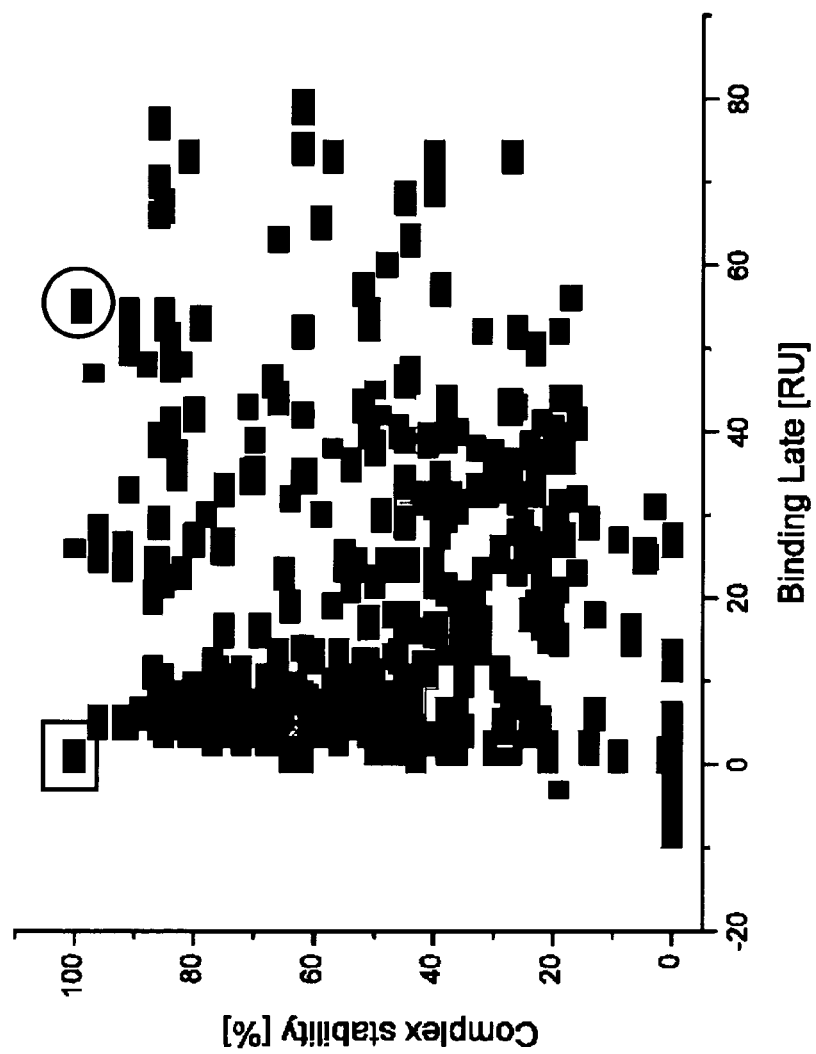
FIG. 2 Binding Late/Complex Stability plot of 549 hybridoma primary cultures: the encircled data spot shows sufficient antigen response signal and 100% complex stability, whereas the enframed data spot shows no sufficient antigen response.

(see FIG. 2). E.g. the encircled data spots show sufficient antigen response signal and 100% complex stability, whereas the enframed data spot shows no sufficient antigen response.

Thus, the top 10% hybridomas according to antigen response signal and complex stability have been selected.

EXAMPLE 4

Hybridoma Cloning and Antibody Production

Anti-PTH antibody producing hybridoma primary cultures, which were selected in Example 3, were subcloned using the cell sorter FACSAria (Becton Dickinson) under the control software V4.1.2. The deposited single clones were incubated under suitable conditions for further proliferation in 24 well plates and were subsequently transferred to the thermodynamic screening process according to Example 5 after having determined the antibody concentration in solution using ELISA methods according to the instruction of the manufacturer.

EXAMPLE 5

Thermodynamic Screening of Secondary Hybridoma Culture Supernatants

Subsequent to the kinetic screening, in which hybridoma cells secreting antibodies with high antibody-antigen-complex stability have been identified, the secreted antibodies were further characterized by a thermodynamic screening employing the determination of the temperature-dependent kinetics in order to determine the antigen-antibody complex thermostability and in order to calculate the thermodynamic properties.

A CM5 sensor series S was mounted into the BIAcore T100 System driven under the control software V1.1.1 and preconditioned by 1 min. injection at 100 µl/min of a mixture comprising 0.1% SDS, 50 mM NaOH, 10 mM HCl and 100 mM $H_3PO_4$.

In case of screening antibodies of murine origin, a polyclonal rabbit anti-murine-IgG antibody (<IgGFCγM>R, Jackson ImmunoResearch Laboratories Inc., USA) at 30 µg/ml was immobilized at 6,000 RU on flow cells 1, 2, 3, 4 with EDC/NHS chemistry according to the manufacturer's instructions using 10 mM sodium acetate buffer pH 4.5 as pre-concentration buffer. Finally, the sensor surface was blocked with ethanolamine.

Figure 3:
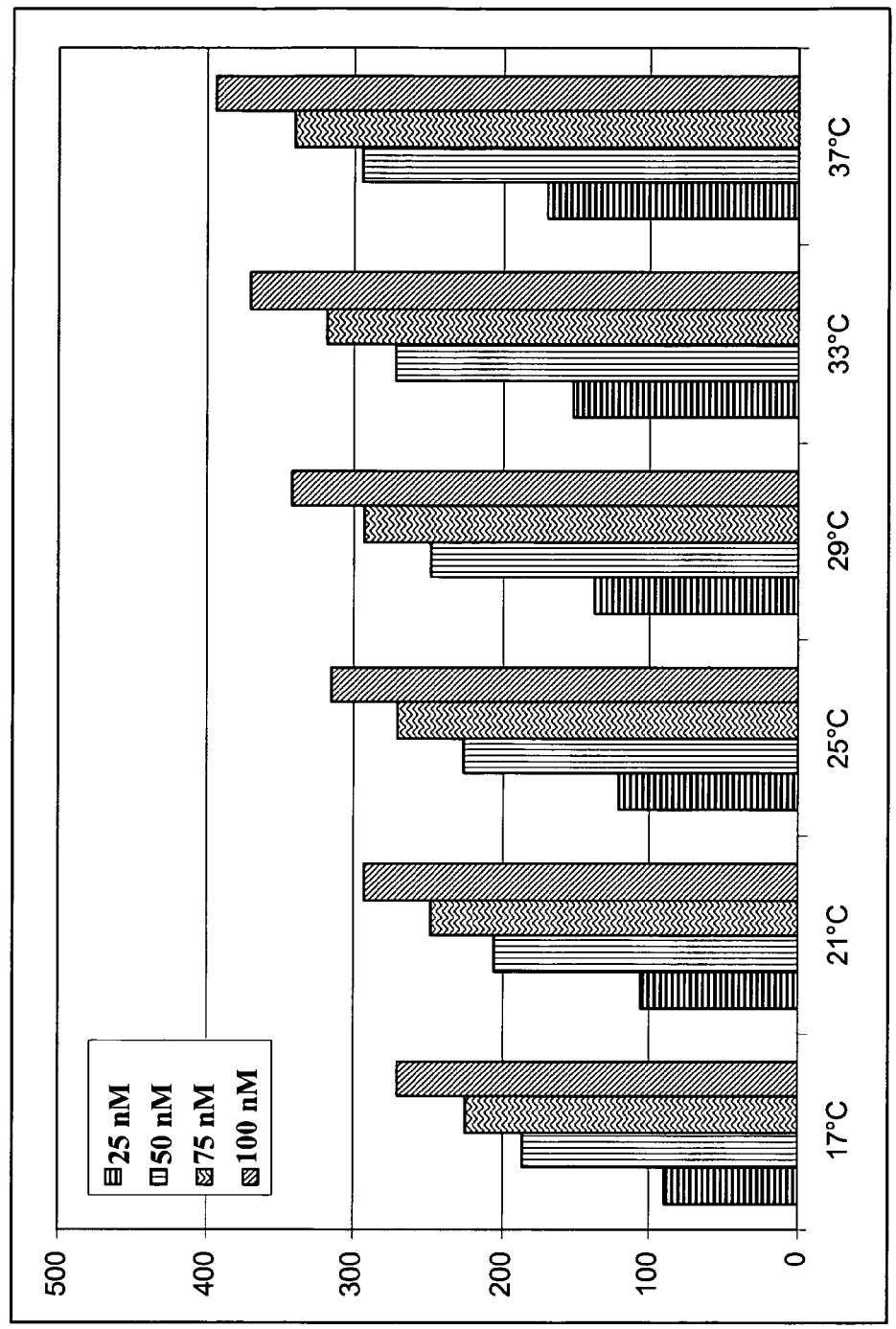
FIG. 3 Secondary antibody response of the <IgGFCγM>R antibody capture system versus the analyte monoclonal anti-TSH antibody at 25 nM, 50 nM, 75 nM and 100 nM and at increasing temperatures.

As reference antibody the monoclonal murine anti-TSH antibody 1.20 (IgG1k, mouse) was temperature-dependently titrated at different concentrations on the above prepared capture system to determine the capture capability of the system (see FIG. 3).

TABLE 3

Response levels of monoclonal murine anti-TSH antibody 1.20 at different concentrations under increasing temperatures on the <IgGFCyM>R antibody capture system.

| | RU at °C.: | | | | | |
|---|---|---|---|---|---|---|
| AK_nM | 17° C. | 21° C. | 25° C. | 29° C. | 33° C. | 37° C. |
| TSH_25 | 91 | 106 | 122 | 137 | 153 | 170 |
| TSH_50 | 187 | 206 | 226 | 248 | 273 | 295 |
| TSH_75 | 225 | 248 | 270 | 293 | 318 | 340 |
| TSH_100 | 270 | 292 | 315 | 342 | 369 | 394 |

These concentration values of the monoclonal murine anti-TSH antibody 1.20 were used as a reference for the calculation of the antibody capturing from the hybridoma cultures in order to achieve similar secondary antibody response levels at different temperatures.

Figure 4:
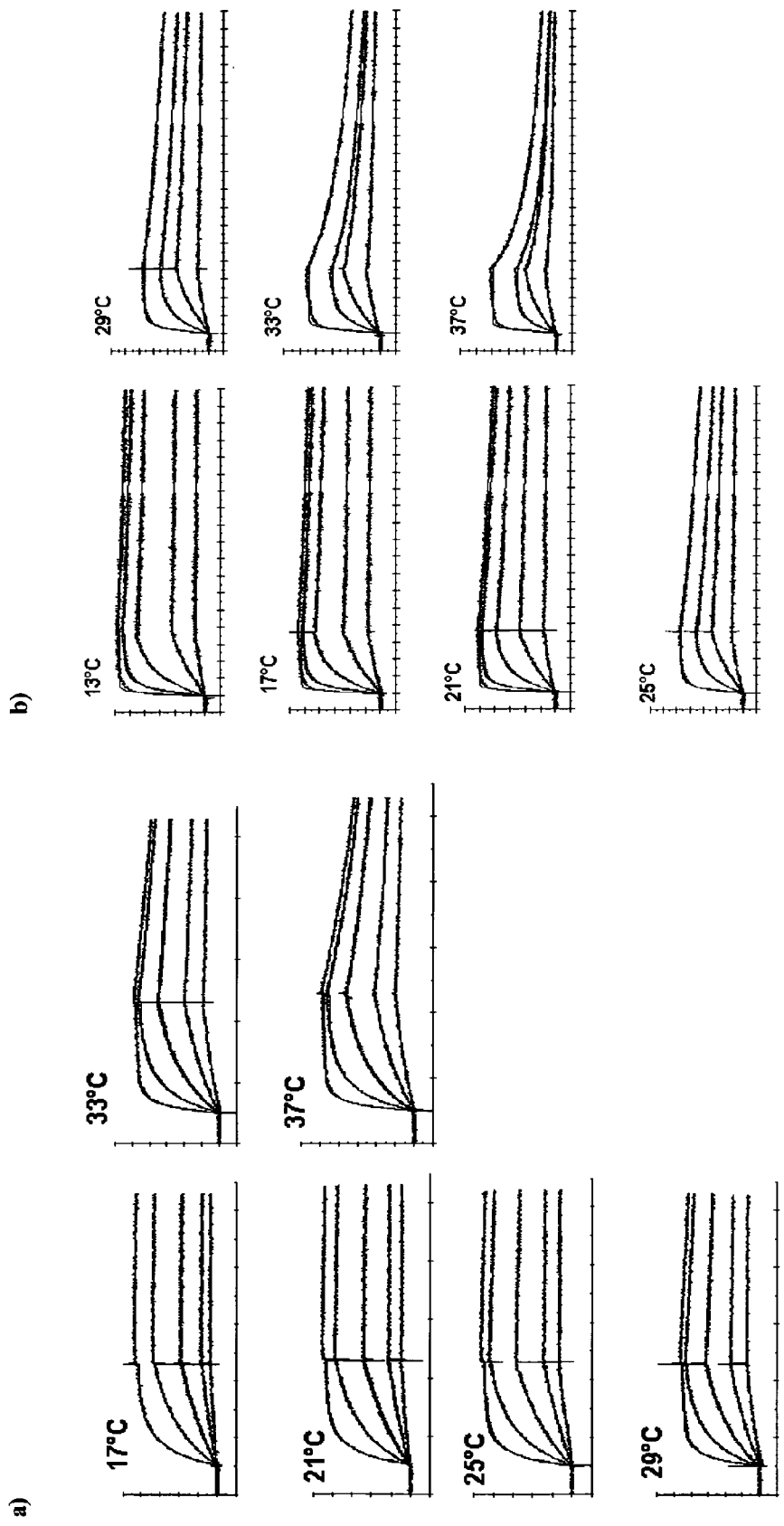
FIG. 4 a) Exemplary concentration-dependent sensograms of the temperature-dependent antibody-PTH interaction of antibody M D1.1. The kinetics were measured in HBS-EP pH 7.4 at 25° C., 3 min. association time, 5 min. dissociation time, fitting according to Langmuir.

Kinetic measurements at different temperatures were performed at 20 µl/min., the flow rate was 30 µl/min., 50 µl/min., 100 µl/min., respectively. The sample injection of recombinant synthetic full length PTH 1-84 (9.4 kDa) was done for 30 sec., 90 sec., 180 sec., respectively, or other suitable injection times in order to achieve ligand saturation or entry into the binding equilibrium during the complex association phase (see FIG. 4 $a$)). The dissociation rate was monitored first for up to 300 sec. and further for 15 min (see FIG. 4 $b$)). The PTH injections were repeated in different concentration steps of at least five concentrations. As control one concentration step was analyzed twice to control the reproducibility of the assay. Flow cell 1 served as a reference. A buffer injection was used instead of an antigen injection to double reference the data by buffer signal subtraction. The capture system was regenerated using 100 mM $H_3PO_4$ by a 2 min. injection at 100 µl/min. The regeneration procedure was optimized to guarantee quantitative surface regeneration also at 13° C., 17° C. and 21° C. At these temperatures the regeneration solution was injected three times whereas at 25° C., 29° C., 33° C. and 37° C. the regeneration solution was injected one time.

The data obtained was evaluated according to a 1:1 binary Langmuir interaction model in order to calculate the association rate constant ka [1/Ms], the dissociation rate constant kd [1/s] and the resulting affinity constant $K_D$ [M] at different temperatures. Thermodynamic equilibrium data was calculated according to the linear form of the Van't Hoff equation. Transition State thermodynamics were calculated according to the Eyring and Arrhenius equations using e.g. the BIAcore T100 evaluation software V.1.1.1 or the program Origin 7sri v. 7.0300.

EXAMPLE 6

Example for the Necessity to Adjust Homogeneous $R_{MAX}$ Values

A BIAcore T100 device was mounted with a CM5 series-S BIAcore sensor, and was immobilized with 6000 RU <IgGFCyM>R (Jackson ImmunoResearch Laboratories Inc., USA) on each flow cell according to the manufacturer's instructions. The non-optimized experiment used 40 nM capture antibody at 20 µl/min., in HBS-EP buffer (0.05% P20). The sample buffer was the system buffer, supplemented with 1 mg/ml CMD.

The antigen was injected after the capturing of the secondary antibody in 6 concentration steps of 1.2 nM, 4 nM, 11 nM, 33 nM, 100 nM and 300 nM, whereby 11 nM were used as a double control and 0 nM were used as reference. The antigen was injected at 100 µl/min for 2 min. association and 5 min. dissociation, followed by a HBS-EP wash of 15 min. at 30 µl/min. and a regeneration with 10 mM glycine pH 1.7 at 3 µl/min for 3 min. Concentration-dependent measurements were done at 4° C., 11° C., 18° C., 25° C., 32° C., and 40° C.

The optimized system was used like described above, but with the exceptions that the antibody to be captured was injected for 3 min. association time at different concentration steps of 100 nM at 15° C., 80 nM at 20° C., 60 nM at 25° C., 50 nM at 30° C., 40 nM at 35° C. and 40 nM at 40° C.

Finally kinetics and thermodynamics were determined using the BIAcore evaluation software.

The invention claimed is:

1. A method for the selection of an antibody from a plurality of antibodies, said method comprising the following steps:
   (a)—determining at the temperatures used in step (e) the signal of a surface plasmon resonance and adjusting the sensor surface so that a constant Rmax value of antigen-antibody binding is obtained at these temperatures, (b)—measuring BL (RU) and SL (RU) by surface plasmon resonance,
(c)—calculating an antigen-complex-stability according to formula (I)

$$\text{antigen-complex-stability} = (1-[BL(RU)-SL(RU)/BL(RU)]) \quad (I)$$

wherein BL denotes a Binding Late reference point set shortly before the antigen's injection ends, and SL denotes a Stability Late reference point set shortly before the end of the complex dissociation phase,
(d)—selecting the antibody with an antigen-complex-stability value greater than 0.95,
(e)—measuring BL(RU) and SL(RU) and calculating the antigen-complex-stability of the antibody of (d) at 17° C., at 21° C., at 25° C., at 29° C., at 33° C., and at 37° C.,
(f)—calculating Transition State thermodynamic properties of the antibody at each temperature of (e) based on equations (II) to (XIII), and
(g)—selecting the antibody when a temperature-dependent acceleration of the antigen complex association rate constant $k_a$ [1/Ms] is detected and a remaining or decreasing antigen complex dissociation rate constant $k_d$ [1/s] is detected, as the temperature increases from 17° C. to 37° C.

2. The method according to claim 1, wherein said thermodynamic properties comprise an enthalpy-driven $\Delta H°\ddagger ass$ antigen complex association phase and a binding entropy $\Delta S°\ddagger ass$ of less than 10 J/K*mol.

3. The method according to claim 1, wherein the antibody selected comprises a dissociation phase showing a negative or nearby zero dissociation activation energy (Eadiss [kJ/mol]), a negative dissociation enthalpy ($\Delta H°\ddagger diss$ [kJ/mol]), and a large negative dissociation entropy ($\Delta S°\ddagger diss$ [kJ/mol]).

4. The method according to claim 2, wherein the antibody selected comprises a dissociation phase showing a negative or nearby zero dissociation activation energy (Eadiss [kJ/mol]), a negative dissociation enthalpy ($\Delta H°\ddagger diss$ [kJ/mol]), and a large negative dissociation entropy ($\Delta S°\ddagger diss$ [kJ/mol]).

* * * * *